(12) United States Patent
Lee et al.

(10) Patent No.: US 11,992,583 B2
(45) Date of Patent: May 28, 2024

(54) DRUG DELIVERY DEVICES AND METHODS

(71) Applicant: TARIS Biomedical LLC, Lexington, MA (US)

(72) Inventors: Heejin Lee, Bedford, MA (US); Karen Daniel, Newton, MA (US); Cheryl Larrivee-Elkins, Framingham, MA (US); Vikas Agarwal, Andover, MA (US); Hong Linh Ho Duc, Weston, MA (US)

(73) Assignee: TARIS Biomedical LLC, Lexington, MA (US)

( * ) Notice: Subject to any disclaimer, the term of this patent is extended or adjusted under 35 U.S.C. 154(b) by 223 days.

(21) Appl. No.: 17/158,322

(22) Filed: Jan. 26, 2021

(65) Prior Publication Data

US 2021/0146013 A1    May 20, 2021

Related U.S. Application Data

(62) Division of application No. 15/306,792, filed as application No. PCT/US2015/030379 on May 12, 2015, now Pat. No. 10,933,170.

(Continued)

(51) Int. Cl.
*A61M 31/00* (2006.01)
*A61K 9/00* (2006.01)
(Continued)

(52) U.S. Cl.
CPC ............ *A61L 29/06* (2013.01); *A61K 9/0034* (2013.01); *A61K 9/14* (2013.01); *A61K 9/20* (2013.01);
(Continued)

(58) Field of Classification Search
CPC .. A61M 31/007; A61M 31/00; A61M 31/002; A61M 2210/16; A61M 27/008;
(Continued)

(56) References Cited

U.S. PATENT DOCUMENTS 4,326,522 A    4/1982  Guerrero et al.
4,871,542 A   10/1989  Villhardt
(Continued)

FOREIGN PATENT DOCUMENTS

| EP | 0059694 B1 | 4/1985 |
| WO | 2005/089671 A1 | 9/2005 |
| WO | 2013/170069 A1 | 11/2013 |

OTHER PUBLICATIONS

Office Action for JP 2016-565288 dated Feb. 7, 2019 (English Translation).

(Continued)

*Primary Examiner* — Laura A Bouchelle
*Assistant Examiner* — Hong-Van N Trinh
(74) *Attorney, Agent, or Firm* — Eversheds Sutherland (US) LLP

(57) ABSTRACT

Drug delivery devices are provided in which much of a drug payload within the device remains within an area proximal to a wall of the device through which the drug must pass for release of the drug from the device into a patient. In one case, the device may include a drug reservoir portion which has a drug reservoir lumen bounded by a reservoir wall having an inner surface; a drug located in the drug reservoir lumen; and a core region which does not comprise the drug, wherein the drug is disposed between the inner surface of the reservoir wall and the core region. The device may be elastically deformable between a first shape suited for inser- (Continued)

tion through a lumen into a body cavity of the patient and a second shape suited to retain the device within the body cavity.

17 Claims, 9 Drawing Sheets

Related U.S. Application Data

(60) Provisional application No. 61/992,179, filed on May 12, 2014.

(51) Int. Cl.
    *A61K 9/14*     (2006.01)
    *A61K 9/20*     (2006.01)
    *A61K 31/167*     (2006.01)
    *A61L 29/06*     (2006.01)
    *A61L 29/14*     (2006.01)
    *A61L 29/16*     (2006.01)

(52) U.S. Cl.
    CPC ............ *A61K 31/167* (2013.01); *A61L 29/14* (2013.01); *A61L 29/16* (2013.01); *A61M 31/00* (2013.01); *A61M 31/002* (2013.01); *A61M 31/007* (2013.01); *A61L 2300/402* (2013.01); *A61M 2205/04* (2013.01); *A61M 2210/16* (2013.01)

(58) Field of Classification Search
    CPC .. A61M 2210/1085; A61M 2210/1089; A61M 25/0041; A61K 9/0053; A61K 9/0065; A61K 9/0068; A61K 9/0034; A61K 9/0036; A61K 9/0039
See application file for complete search history.

(56) References Cited

U.S. PATENT DOCUMENTS

| | | | |
|---|---|---|---|
| 6,171,298 B1 | 1/2001 | Matsuura et al. | |
| 6,183,461 B1 | 2/2001 | Matsuura et al. | |
| 8,211,085 B2 | 7/2012 | Devonec | |
| 8,343,516 B2 | 1/2013 | Daniel et al. | |
| 8,679,094 B2 | 3/2014 | Cima et al. | |
| 8,690,840 B2 | 4/2014 | Lee et al. | |
| 9,017,312 B2 | 4/2015 | Lee et al. | |
| 9,107,816 B2 | 8/2015 | Lee et al. | |
| 9,283,361 B2 | 3/2016 | DiCesare et al. | |
| 9,457,176 B2 | 10/2016 | Lee et al. | |
| 9,492,266 B2 | 11/2016 | Hutchins, III et al. | |
| 2004/0230119 A1* | 11/2004 | Brustad | A61L 31/146 600/442 |
| 2005/0209556 A1 | 9/2005 | Tresco et al. | |
| 2007/0161967 A1 | 7/2007 | Fischer, Jr. et al. | |
| 2007/0202151 A1* | 8/2007 | Lee | A61M 31/002 424/426 |
| 2008/0004578 A1* | 1/2008 | Hixon | A61F 2/04 604/326 |
| 2009/0187254 A1* | 7/2009 | Deal | A61M 27/008 604/8 |
| 2010/0330149 A1 | 12/2010 | Daniel et al. | |
| 2010/0331770 A1* | 12/2010 | Lee | A61M 31/007 221/199 |
| 2011/0230950 A1 | 9/2011 | Knapp | |
| 2014/0276636 A1 | 9/2014 | Lee et al. | |
| 2016/0008271 A1 | 1/2016 | Lee | |
| 2016/0199544 A1 | 7/2016 | Lee et al. | |

OTHER PUBLICATIONS

Partial European Search Report for counterpart EP Application No. 20211066.4 dated May 7, 2021 (15 pages).

* cited by examiner

DRUG DELIVERY DEVICES AND METHODS

CROSS-REFERENCE TO RELATED APPLICATIONS

This application is a divisional of U.S. application Ser. No. 15/306,792, filed Oct. 26, 2016, which is the national stage of PCT/US2015/030379, filed May 12, 2015, which claims priority to U.S. Provisional Application No. 61/992,179, filed May 12, 2014, all of which are incorporated herein by reference.

TECHNICAL FIELD

This disclosure is generally in the field of drug delivery devices for insertion into a patient for controlled release of drug to the patient, wherein the devices may be capable of providing more complete release of a drug payload from the device in vivo to the patient's body over a treatment period, which may enable one to release desired dosages of the drug with a smaller total drug payload.

BACKGROUND

In the interest of patient safety, many drug delivery devices (e.g., implantable drug delivery devices) are loaded with a significant amount of excipients to minimize the amount of potent drug loaded into the devices. It is often difficult, however, to identify an excipient that does not negatively impact drug stability and/or the drug release profile. Maintaining the homogeneity of a drug and excipient mixture also can be difficult, especially when the mixture contains a lower percentage of the drug.

In many current reservoir type tubular drug delivery devices that rely on drug diffusion through a polymeric reservoir wall, the reservoirs are often filled entirely with a drug or drug and excipient mixture in order to achieve a desired drug release rate. If, however, the drug release rate is insufficient to deplete a significant amount of drug loaded into the reservoir at the end of the treatment period, then several potential problems may arise, including dose dumping, additional drug release caused by delayed device removal, wasted active pharmaceutical ingredient (API), and/or difficulty in measuring the amount of drug released while in use. These problems may adversely impact patient safety and may become more serious when the devices contain drugs of higher potency.

It therefore would be desirable to provide drug delivery devices that can mitigate or avoid one or more of these potential problems. For example, it would be desirable to provide devices and methods that give a more complete release of a drug payload over a desired therapeutic period, so as to reduce the amount of drug required in the device and to reduce the amount of unreleased (e.g., wasted) drug in the device, without negatively impacting the amounts and/or rates of drug released.

BRIEF SUMMARY

In one aspect, a drug delivery device is provided for insertion into the body of a patient, and the device includes a drug reservoir portion which comprises a drug reservoir lumen bounded by a reservoir wall having an inner surface; a drug formulation located in the drug reservoir lumen, wherein the drug formulation comprises a drug; and a core region which does not comprise the drug, wherein the drug formulation is disposed between the inner surface of the reservoir wall and the core region.

In another aspect, a drug delivery device is provided for insertion into the body of a patient, and the device includes a drug reservoir portion which comprises a drug reservoir lumen bounded by reservoir walls which comprise a water permeable polymeric material; and a drug formulation which comprises a drug and which substantially fills the drug reservoir lumen, wherein the drug reservoir lumen has a ribbon shape such that a substantial portion of the drug formulation is adjacent to the reservoir wall to facilitate diffusion of the drug through the reservoir walls.

In still another aspect, a drug delivery device is provided for insertion into the body of a patient, and the device includes a drug reservoir portion which comprises a lumen bounded by a reservoir wall having an interior portion which includes an inner surface; a drug formulation, which comprises a drug, located in the interior portion of the reservoir wall; and a core region in the lumen which does not comprise the drug. The interior portion of the reservoir wall may be in the form of a coating layer in which the drug formulation is dispersed.

The devices, in a preferred embodiment, are elastically deformable between a first shape suited for insertion through a lumen into a body cavity of the patient and a second shape suited to retain the device within the body cavity. For example, the lumen may be the urethra, and the body cavity may be the urinary bladder.

BRIEF DESCRIPTION OF THE DRAWINGS

Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Figure 1A:
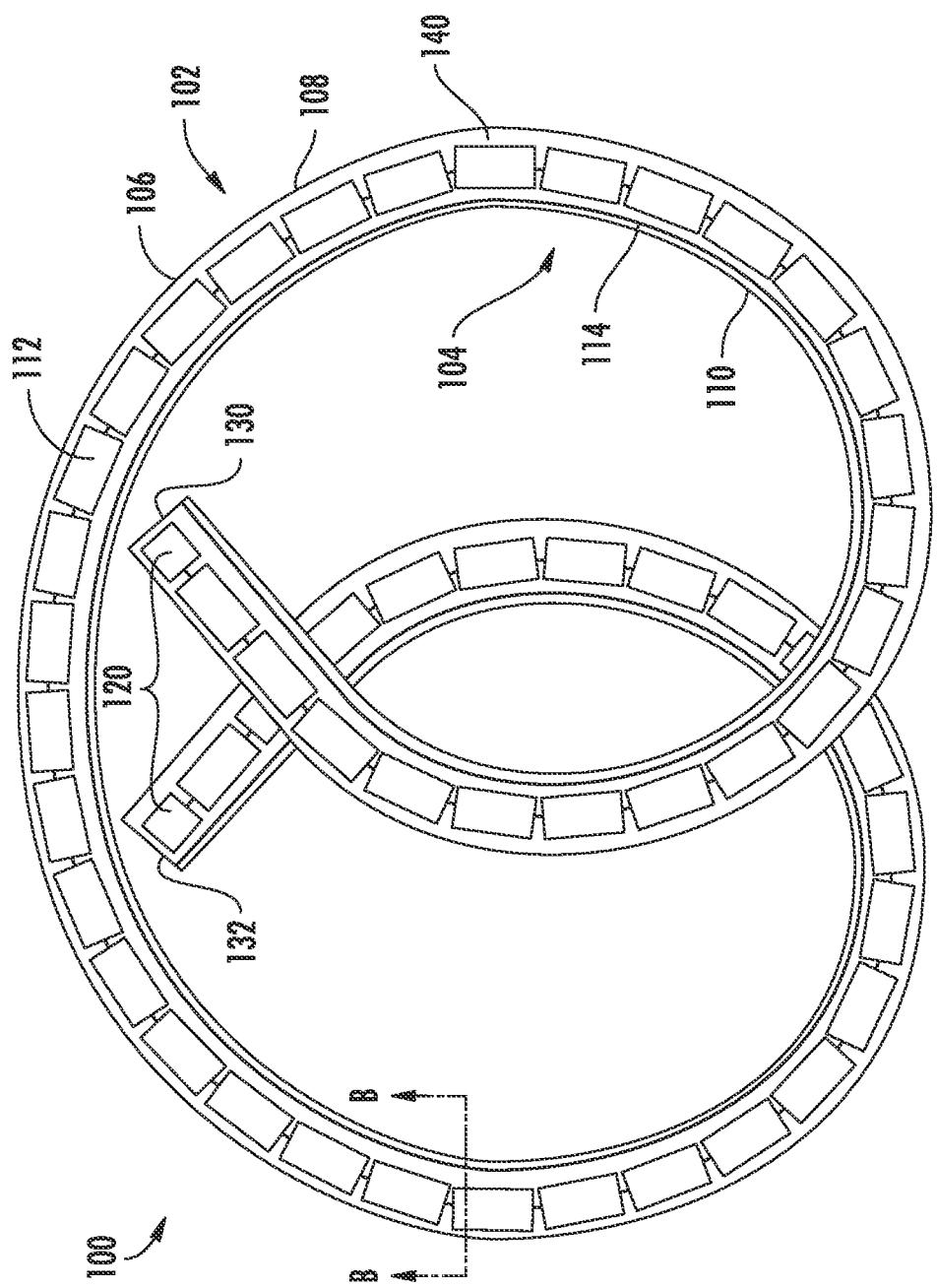
FIG. 1A is a plan view of one embodiment of a drug delivery device having a core region which includes a plurality of structural objects, as described herein.

The drug delivery devices provided herein address one or more of the above-described problems because the drug delivery devices provided herein have configurations that control the location of drug within the devices. By such selective positioning of drug within the devices, for example by positioning all of the drug of the drug payload on board the device at or very near a reservoir wall through which drug release occurs, less drug may be needed in the device to provide a given release profile, as compared to some other drug delivery device designs. Such a drug payload also advantageously may reduce the amount of unreleased drug waste and/or reduce dose dumping risks, and may also beneficial provide a smaller and hence better tolerated device from the perspective of the patient in whom the device is implanted/inserted.

The present devices are generally reservoir based. As used herein, the term "reservoir-based" means that the drug initially is contained in a defined reservoir of a device, not in a matrix material in which the drug is comingled. That is, the reservoir is a container, vessel, or lumen; it is not a matrix material. That is, the drug reservoir, which may be the central lumen of annular tube, is defined/bound by a tube wall or other wall (or portion thereof) of the device that controls release of solubilized drug therefrom, e.g., by diffusion therethrough.

In one aspect, the devices provided herein are configured to ensure that at least a majority of the drug formulation within the devices remains within an area proximal to the wall(s) of the devices through which the drug must pass (e.g., by diffusion) for release of the drug from the device. In other words, the devices are advantageously are configured to reduce or minimize the distances between the drug and the inner surface of the wall(s) of the device, wall(s) which define the reservoir in which the drug payload is initially confined.

In one embodiment, this configuration is achieved by disposing a drug formulation between a reservoir wall of a drug reservoir lumen and a core region. The core region does not contain any of the initial drug payload. The core region may be empty space or may comprise one or more structures (objects). In preferred embodiments, the drug is in a solid form, such as tablets, powder, granules, or an annular dosage form (e.g., made by molding the drug into an annular shape).

In another embodiment, the configuration is achieved by disposing a drug formulation in a ribbon-shaped drug reservoir lumen. The flat nature of the ribbon-shaped drug reservoir lumens ensures that a majority of the drug formulation remains within an area proximal to the devices' walls. In some embodiments, the ratio of the width of the ribbon-shaped drug reservoir lumen when viewed in cross-section to the maximum height of the ribbon-shaped drug reservoir lumen when viewed in cross-section is at least 4:1, such as 7:1 or 10:1.

The drug delivery devices also may include a retention frame portion. The retention frame portion, in some embodiments, includes a retention frame lumen and a retention frame disposed in the retention frame lumen. Such a retention frame is typically in the form of an elastic wire having a shape that is coiled in the absence of a compressive load.

Figure 1B:
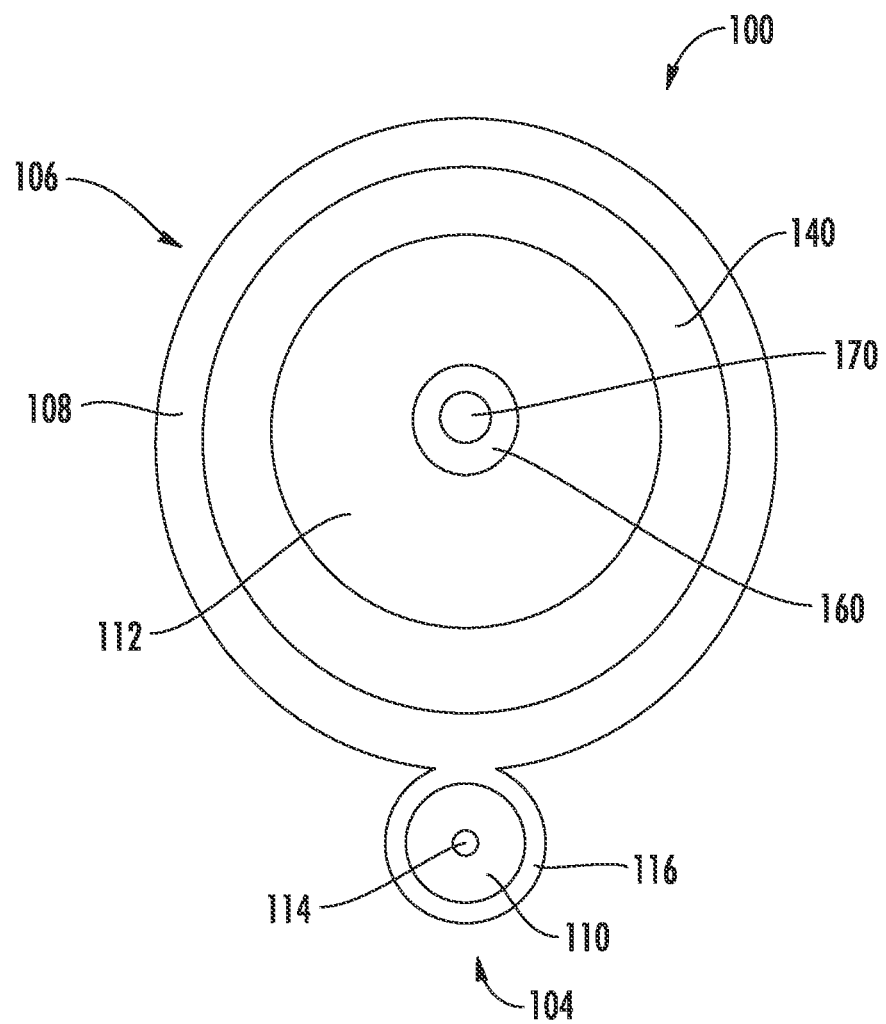
FIG. 1B is a cross-sectional view of the drug delivery device shown in FIG. 1A, taken along line B-B.

One embodiment of a drug delivery device 100 is shown in FIGS. 1A-1B. The device 100 includes a drug reservoir portion 102 which may include an annular tube shaped body 106 formed from an elastomeric material. The device 100 also includes a retention frame portion 104 that includes a retention portion wall 116 having an inner surface which defines a retention frame lumen 110. A retention frame 114 is disposed within the retention frame lumen 110.

The retention portion wall 116 may be integrally formed with the annular tube shaped body 106. The retention frame 114 may be an elastic wire formed to maintain, e.g., biased into, a coiled shape, so as to be effective to hold the device 100 in the illustrated overlapping, or coiled shape. The device 100 is elastically deformable between a first shape suited for insertion through a body lumen of a patient into a body cavity of the patient and a second shape suited to retain the device within the body cavity. In the illustrated embodiment of FIG. 1A, the device 100 is in the second shape, which is induced by the retention frame 114 in the absence of a compressive load to elastically deform the device into the first shape.

The tube 106 includes an elongated reservoir wall 108, the inner surface of which defines a drug reservoir lumen. The drug reservoir lumen includes a core region that is filled with a plurality of cylindrical structural objects 112 and a drug formulation 140 which includes a drug. The structural objects 112 contain no drug. The function of the structural objects 112 is to occupy the core region so that the drug formulation 140 is positioned adjacent to the reservoir wall 108. In this way, the drug formulation 140 is disposed between the inner surface of the reservoir wall 108 and the core region. The tube 106 includes opposed ends 130 and 132, which may be sealed with sealing structures 120. One or both of the sealing structures 120 may be solid and impermeable to drug. Alternatively, the sealing structures 120 may include a defined through-hole or aperture for drug release by diffusion or osmotic pressure, or the sealing structures may include a drug-permeable wall for drug release by diffusion therethrough. In some embodiments, release of the drug in vivo occurs by diffusion or osmotic pressure through an aperture in the reservoir wall. In some embodiments, release of the drug in vivo occurs by diffusion through reservoir wall, for example where the reservoir wall is formed at least in part of silicone, polyurethane, and/or another drug-permeable polymeric material.

As shown in FIG. 1B, the drug delivery device 100 includes the drug reservoir lumen is filled with a structural object 112 in the central area, i.e., in the core region, and a drug formulation 140 occupies the region between the structural object 112 and the inner surface of the reservoir wall 108. In the illustrated embodiment, the structural object 112 includes a through-hole 160 through which a tether 170 passes. The tether 170 may be used to secure the structural objects together in a manner that does not impede the elastic deformation of the device. In other embodiments, the structural objects do not include a through-hole or tether.

In an alternative embodiment, which is not shown, the retention frame portion of device 100 is omitted, and the tether 170 is replaced with a retention frame 114, in the form of an elastic wire. In this way, the retention shape of the device is imparted via an elastic wire in the core region of the drug reservoir portion.

The drug delivery devices provided herein can be inserted into a lumen or body cavity of a patient, such as the urinary bladder, uterus, or other luminal site, for local or regional administration of one or more drugs to the tissues at the sited. The drug delivery devices provided herein also can also be configured for subcutaneous, intramuscular, intraocular, or intraperitoneal implantation.

Devices Having a Core Region

In one aspect, the drug delivery devices comprise a drug reservoir lumen bounded by a reservoir wall, a drug formulation, and a core region, wherein at least a portion of the drug formulation is disposed between the reservoir wall and the core region. The core region preferably is a biocompatible and inert material.

In some embodiments, the core region is essentially empty space. For example, the empty space may include air, one or more other gases, or a combination thereof. The air or other gases may be inert. The air or other gases may be chosen to influence the buoyancy of the devices. The air or other gases may be chosen to influence the amount of moisture in the device prior to use. The air or other gases also may be drawn out of the devices. If the device is made of an elastomeric material, drawing the air out of the device after filling it with drug may cause the drug reservoir lumen to collapse, thereby reducing the overall size and cross-sectional diameter or width of the device. This may be useful for fitting the devices into a catheter-like insertion system, especially when the device contains multiple drug reservoir lumens.

In one embodiment, the core region comprises a filler material. The filler material may be an excipient material, which may be in the form of a powder.

In another embodiment, the core region includes one or more structural objects. The structural object may be formed of essentially any material that does not react with or interfere with release of the drug. It may be formed of pharmaceutical excipient materials, or it may be formed of other materials, such as metals, polymers, ceramics, or combinations thereof. It may be inert. It may be formed of a bioresorbable material, the biodegradation of which does not interfere with release of the drug from the device. The structural object may be made by a molding process known in the art. In a preferred embodiment, the structural object is substantially impermeable to the drug. The structural object may be coated with a drug- and/or water-impermeable coating. In one embodiment, such a coating comprises Parylene C.

In embodiments, the structural object may be substantially flexible to facilitate insertion or implantation of the device as described herein.

In embodiments, the structural object may spherical, ellipsoidal, or substantially cylindrical. The structural object may have a cross-sectional shape that substantially conforms to the inner shape of the drug reservoir lumen.

In still another embodiment, the core region includes a combination of empty space and a structural object. For example, the empty space may have a tether passing through a portion of the empty space.

In certain embodiments, the object is a monolithic structure. The length of the monolithic object, in one embodiment, is substantially the same as the length of the drug reservoir lumen. The length of the monolithic object, in another embodiment, is less than the length of the drug reservoir lumen. The object may be threaded or have a helical structure, which may facilitate the placement of the object in the device and/or the loading of a drug into the drug reservoir lumen. For example, a drug may be placed in the threads of the object before the object is disposed in the drug reservoir lumen. As another example, a loosely filled drug powder can be loaded into the drug reservoir lumen, and then a screw-like object passed into/through the powder in the center of the drug reservoir lumen (e.g., along its central axis), compacting the powder and displacing the powder toward the walls of the reservoir lumen.

In another embodiment, the device has a core region that includes a plurality of structural objects. The plurality of objects, or at least a portion thereof, may be tethered to each other. The plurality of objects may be tethered to each other by any means known in the art, including a string of a biocompatible material. The tether may be a metallic wire or a polymeric fiber, or one or more bundles of such wires or fibers. The plurality of structural objects may have a hole passing through their structures to accommodate the tether. The tether may be used to prevent the objects from migrating within the drug delivery device. The plurality of structural objects may be affixed to the tether, allowed to slide freely along the tether, or a combination thereof. In some embodiments, the plurality of objects are tethered in a manner that permits the tethered plurality of objects to form a curved shape to permit the insertion, deployment, or implantation of the drug delivery devices as provided herein.

In one variation of the foregoing embodiment (not shown) the tether comprises an elastic wire, such that the tether functions as a retention frame and possesses a coiled retention shape, for example. Such as tether retention frame may complement or replace the need for and use of a separate retention frame lumen and retention frame disposed therein.

The structural object of the core region may be affixed to the drug reservoir lumen (i.e., the wall of the drug reservoir lumen) at one or more locations. In embodiments, the structural object is affixed to the reservoir wall along all or a portion of the longitudinal axis of the drug reservoir lumen. The structural object may be directly affixed to the reservoir wall. The structural object may include a ridge or other substantially raised portion that may be directly affixed to the reservoir wall. If the device includes a plurality of structural objects, then all or a portion of the plurality of structural objects may be directly affixed to the reservoir wall. If the device includes a plurality of structural objects, then all or a portion of the plurality of structural objects may include a ridge or other substantially raised portion that may be directly affixed to the reservoir wall. If a plurality of structural objects is tethered to one another, then the tether may be affixed to the reservoir wall and/or to an end plug, in some embodiments. The structural object may be affixed to the reservoir wall by any means known in the art, including use of a biocompatible adhesive, tying, clipping, or otherwise mechanically clamping or adhering the tether to the wall defining the drug reservoir lumen or to an end plug, or a combination thereof.

In some embodiments, the drug reservoir body and the structural object are made from the same materials. In other embodiments, the drug reservoir lumen and the object may be manufactured as a continuous material, thereby eliminating the need to affix the core region to the drug reservoir lumen.

Figure 2:
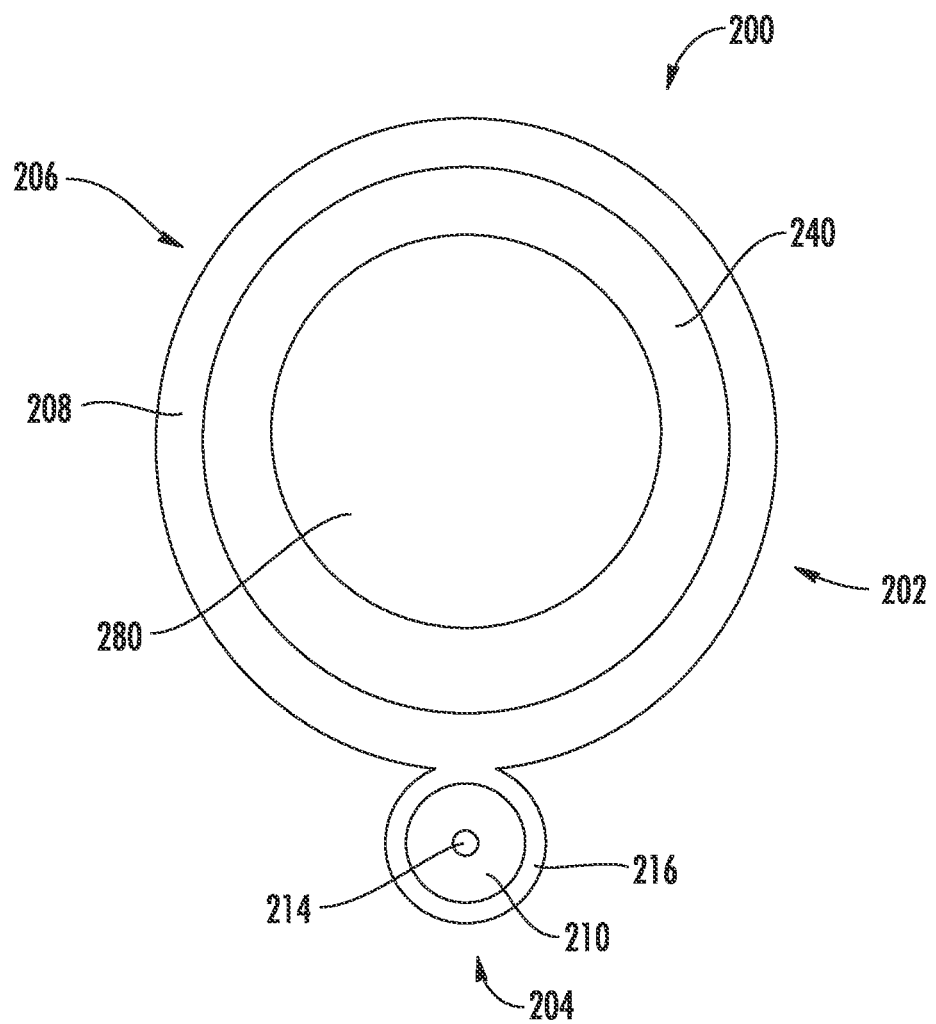
FIG. 2 is a cross-sectional view of another embodiment of a drug delivery device having a core region which includes an empty space, as described herein.

In another embodiment, which is illustrated in FIG. 2, the core region consists essentially of empty space. Here, the drug delivery device 200 includes a drug reservoir portion 202 which includes an annular tube shaped body 206 having a reservoir wall 208 that defines a drug reservoir lumen. The drug reservoir lumen is filled with an empty core region 280 and a drug formulation 240 positioned between the empty core region 280 and the inner surface of the reservoir wall 208. The empty core region may be evacuated and therefore essentially devoid of matter, or the empty core region may contain a gas, such as a biocompatible, substantially inert gas. Examples of such gases include air, nitrogen, or a halogen. The air or other gas may influence the buoyancy of the device in the urinary bladder. For example, the air or other gas may facilitate the device to be buoyant in urine in the bladder, which can aid retention of the device in the bladder and/or facilitate device tolerability in the bladder. The drug formulation 240 may be in the form of a powder, granules, or annular shaped solid dosage unit or units. In one embodiment, the drug formulation 240 is in the form of a hollow tablet. Such a hollow tablet may be made by molding, such as compression molding. The device 200 also includes a retention frame portion 204 that includes a retention portion wall 216 having an inner surface which defines a retention frame lumen 210. A retention frame 214 is disposed within the retention frame lumen 210.

Figure 3:
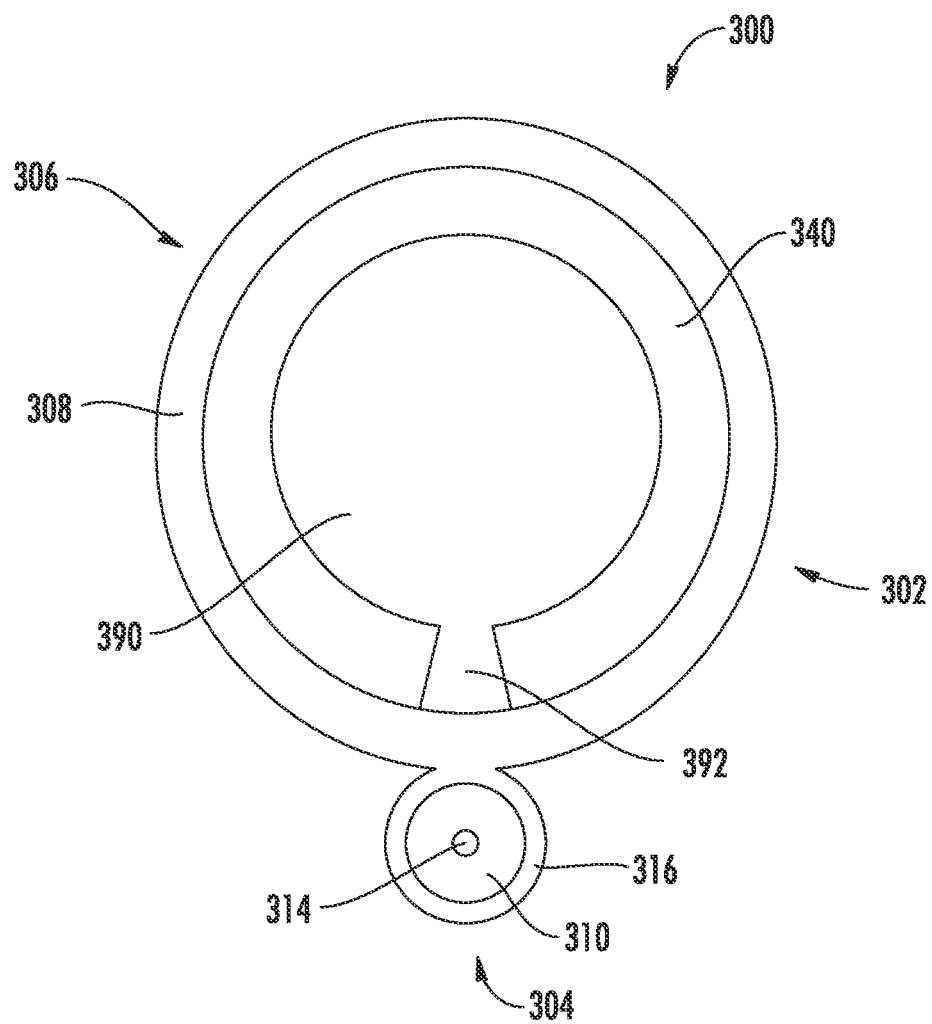
FIG. 3 is a cross-sectional view of yet another embodiment of a drug delivery device having a core region which includes a structural object attached to the reservoir wall, as described herein.

Another embodiment of a drug delivery device having a core region is depicted in FIG. 3. Here, the drug delivery device 300 includes a drug reservoir portion 302 which includes an annular tube shaped body 306 having a reservoir wall 308 that defines a drug reservoir lumen. The drug reservoir lumen is filled with a core region 390 and a drug formulation 340. The drug formulation 340 is positioned between the core region 390 and the inner surface of the reservoir wall 308. The core region 390 is a substantially cylindrical, polymeric, monolithic object that includes a ridge 392 that is affixed to a portion of the inner surface of the reservoir wall 308 extending in a direction parallel to the longitudinal axis of the drug reservoir lumen. The drug formulation 340 may be in the form of a powder, granules, or C-shaped solid dosage unit or units. The device 300 also includes a retention frame portion 304 that includes a retention portion wall 316 having an inner surface which defines a retention frame lumen 310. A retention frame 314 is disposed within the retention frame lumen 310.

In one variation of the foregoing embodiment (not shown) the core region is configured to provide the retention shape function for the device. That is the substantially cylindrical, polymeric, monolithic object 390 may be formed of appropriate materials and dimensioned to impart the required elasticity and spring constant the device requires and which would otherwise be provided by the retention frame portion 304. In such an embodiment, the retention frame portion 304 may be omitted. For example, the object 390 may be molded or thermo shape set to have the second shape, e.g., a bladder retention shape.

Figure 4:
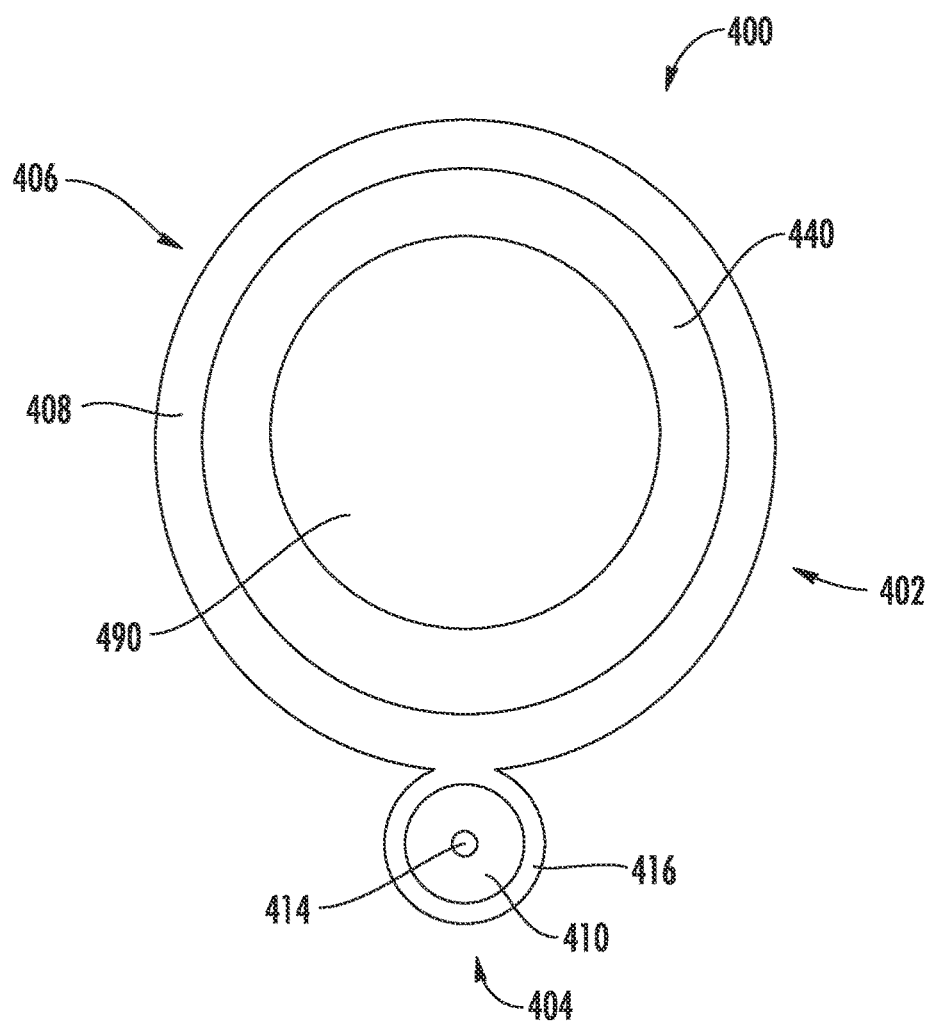
FIG. 4 is a cross-sectional view of still another embodiment of a drug delivery device having a core region which includes a structural object unattached to the reservoir wall, as described herein.

FIG. 4 illustrates yet another embodiment of a drug delivery device having a particular core region. Here, the drug delivery device 400 includes a drug reservoir portion 402 which includes an annular tube shaped body 406 having a reservoir wall 408 that defines a drug reservoir lumen. The drug reservoir lumen is filled with a core region 490 and a drug formulation 440. The drug formulation 440 is positioned between the core region 490 and the inner surface of the reservoir wall 408. The core region 490 is a substantially cylindrical, polymeric, monolithic object which is unattached to the inner surface of the reservoir wall 408 and which extends in a direction parallel to the longitudinal axis of the drug reservoir lumen. The drug formulation 440 may be in the form of a powder, granules, or an annular-shaped solid dosage unit or units. The device 400 also includes a retention frame portion 404 that includes a retention portion wall 416 having an inner surface which defines a retention frame lumen 410. A retention frame 414 is disposed within the retention frame lumen 410.

In one variation of the foregoing embodiment (not shown) the core region is configured to provide the retention shape function for the device. That is the substantially cylindrical, polymeric, monolithic object 490 may be formed of appropriate materials and dimensioned to impart the required elasticity and spring constant the device requires and which would otherwise be provided by the retention frame portion 404. In such an embodiment, the retention frame portion 404 may be omitted. For example, the structural object 490 may be molded or thermo shape set to have the second shape, e.g., a bladder retention shape.

Figure 5:
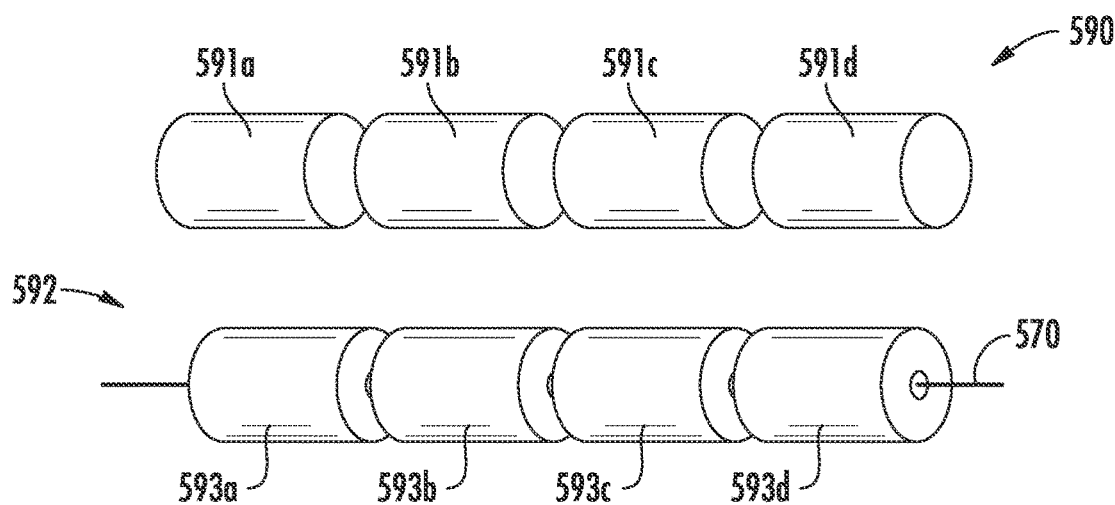
FIG. 5 depicts perspective views of two embodiments of alternative core region configurations, which comprise a plurality of structural objects.

FIG. 5 illustrates alternative core regions that could be substituted for the core region 490 of FIG. 4. Core region 590 consists of a plurality of structural objects 591a/b/c/d, rather than a single monolithic structure. The plurality of structural objects 591a/b/c/d may be cylindrical and aligned end-to-end within a drug reservoir lumen, free to move with respect to one another in a limited manner constrained by the reservoir wall. Core region 592 consists of a plurality of structural objects 593a/b/c/d, each of which includes a through-hole, and which are connected by tether 570 which passes through the through-holes of the objects. Optionally, one or both ends of the tether 570 may be secured to the reservoir wall and/or to one or both end plugs of the drug reservoir portion. As illustrated in FIG. 5, core region 590 and core region 570 each include four structural objects; however, in other embodiments, these core regions may include more or less than four objects. For example, core regions 570 and 590 could include from 10 to 100, from 20 to 60 or other numbers of structural objects. In addition, in other embodiments, the structural objects 591a/b/c/d and 593a/b/c/d can be in shapes other than substantially cylindrical. As with the other tether embodiments described above, the tether 570 may be substituted with an elastic wire imparting a retention shape to the drug delivery device.

In another embodiment of the drug delivery device, the drug may be partly or completely provided within an interior portion of the reservoir wall, in contrast to being located essentially entirely on top of the inner surface of the material defining the reservoir walls that surround the reservoir lumen, or between the inner surface and the core region. For example, in one embodiment, the drug delivery device includes a drug reservoir portion which comprises a lumen bounded by a reservoir wall having an interior portion which includes an inner surface; a drug formulation, which comprises a drug, located in the interior portion of the reservoir wall; and a core region in the lumen which does not comprise the drug. In one case, for example, the interior portion of the reservoir wall is in the form of a coating layer in which the drug formulation is dispersed. For instance, the device body may include an elastomeric annular tube (e.g., of silicone or another water-permeable and drug permeable elastomeric material) and the interior of the tube may be coated with a thin layer of the same or a different elastomeric material in which a drug is dispersed. In this way, the reservoir wall may be considered to include an outer, drug-free portion and an interior portion that includes at least some or all of the drug. This embodiment advantageously would secure the drug payload at a position at/near to reservoir wall, leaving the core region unoccupied by the drug formulation. The device may be elastically deformable between a first shape suited for insertion through a lumen into a body cavity of the patient and a second shape suited to retain the device within the body cavity.

Drug Delivery Devices Having a Ribbon-Shaped Drug Reservoir Lumen

In another aspect, the drug delivery device has a non-cylindrical drug reservoir lumen and non-cylindrical walls defining the reservoir lumen, which are configured to place all or most of the drug payload in close proximity to the wall(s) defining the drug reservoir lumen. In a preferred embodiment, the device includes relatively flat, or ribbon-shaped, drug reservoir lumen, in which a drug formulation is disposed, which may increase the surface area of the device wall bounding the drug reservoir lumen so as to enhance the available surface area through which drug from the drug payload may diffuse. The ribbon-shaped drug reservoir lumen may be seen as a narrow channel when viewed in cross-section (normal to the longitudinal axis of the device). When viewed in cross-section, the channel may be substantially planar, or it may have a spiral shape, a zigzag, serpentine, or winding shape, or other shape that enables the device to have a high profile for retention of the device in the bladder or other body cavity of a patient and a low-profile to permit insertion or implantation of the device into the patient. The devices having ribbon-shaped drug reservoir lumens may be configured like the device shown in FIG. 1A.

In some embodiments, the ratio of the width of the ribbon-shaped drug reservoir lumens when viewed in cross-section to the maximum height of the ribbon-shaped drug reservoir lumens when viewed in cross-section is at least 4:1. In other embodiments, the ratio of the length of the ribbon-shaped drug reservoir lumens when viewed in cross-section to the maximum width of the ribbon-shaped drug reservoir lumens when viewed in cross-section is at least 7:1. In further embodiments, the ratio of the length of the ribbon-shaped drug reservoir lumens when viewed in cross-section to the maximum width of the ribbon-shaped drug reservoir lumens when viewed in cross-section is at least 10:1.

Figure 6:
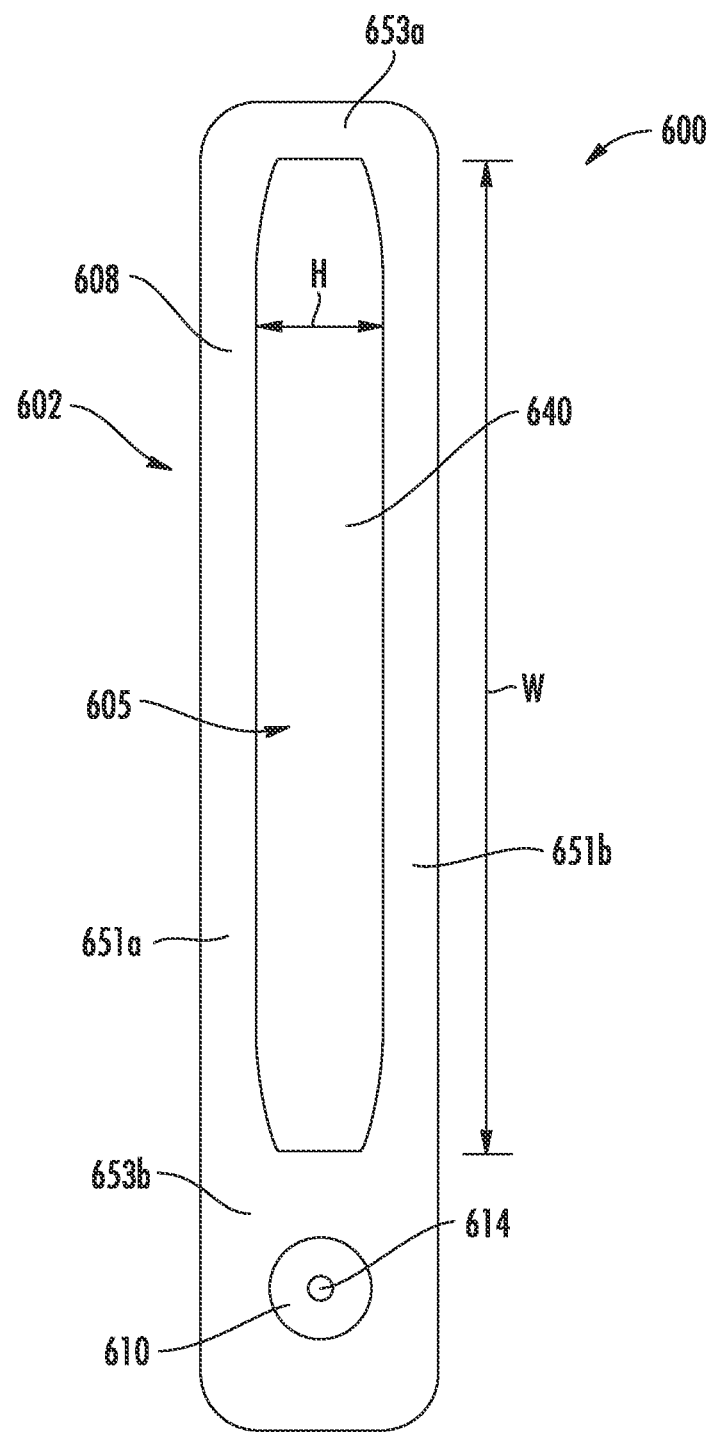
FIG. 6 is a cross-sectional view of one embodiment of a drug delivery device having a ribbon-shaped drug reservoir lumen, as described herein. (The length of the ribbon can be considered as going into and out of the page.)

One embodiment of a drug delivery device having a ribbon-shaped drug reservoir lumen is depicted at FIG. 6. Drug delivery device 600 has a drug reservoir portion 602 which has an elongated body portion that includes a ribbon-shaped drug reservoir lumen 605. The lumen 605 is defined by and within reservoir walls 608, and the lumen 605 is substantially or completely filled with a drug formulation 640. The reservoir walls 608 include opposed long sidewalls 651a and 651b which are connect to (and typically integrally formed with) opposed short sidewalls 653a and 653b. Short sidewall 653b, in the illustrated embodiment, is thicker than short sidewall 653a and includes a retention frame lumen 610 in which retention frame 614 is disposed. In preferred embodiments, the dimensions of the sidewalls are such that the ratio of the maximum width W of the ribbon-shaped drug reservoir lumen 605 (when viewed as in FIG. 6) to the maximum height H of the ribbon-shaped drug reservoir lumens 605 (when viewed as in FIG. 6) is at least 4:1. In certain other preferred embodiments, the W:H ratio is at least 7:1 or at least 10:1, to thereby locate the entire drug formulation 640 payload substantially near the reservoir walls.

Figure 7:
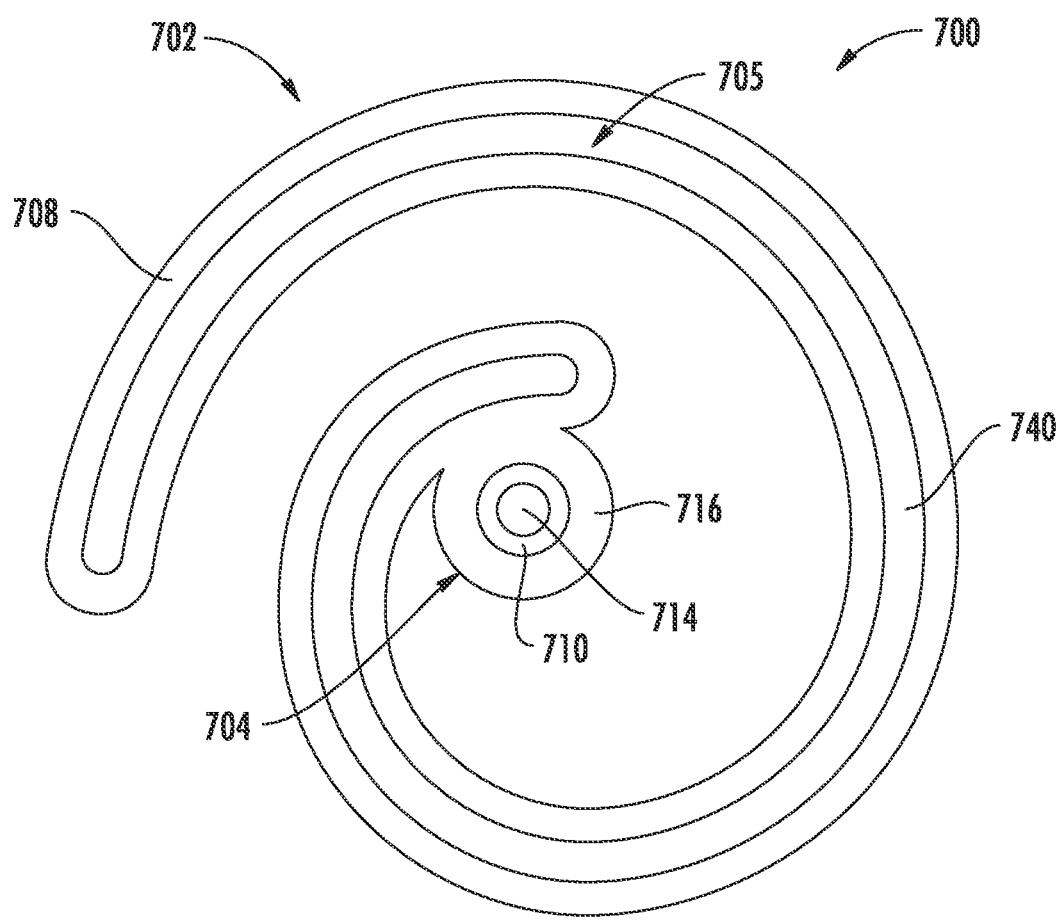
FIG. 7 is a cross-sectional view of another embodiment of a drug delivery device having a ribbon-shaped drug reservoir lumen, wherein the reservoir walls and lumen are in a spiral configuration.

Another embodiment of a drug delivery device having a ribbon-shaped drug reservoir lumen is depicted in FIG. 7. Drug delivery device 700 has a drug reservoir portion 702 which has an elongated body portion that includes a drug reservoir lumen 705. The drug reservoir lumen is ribbon-shaped and the ribbon shaped lumen (as well as the reservoir walls defining it) is in an overall spiral shape. The lumen 705 is defined by and within reservoir walls 708, and the lumen 705 is substantially or completely filled with a drug formulation 740. The drug delivery device 700 also includes a retention frame portion 704 that includes a retention wall 716 having an inner surface which defines a retention frame lumen 710. A retention frame 714 is disposed within the retention frame lumen 710.

Figure 8:
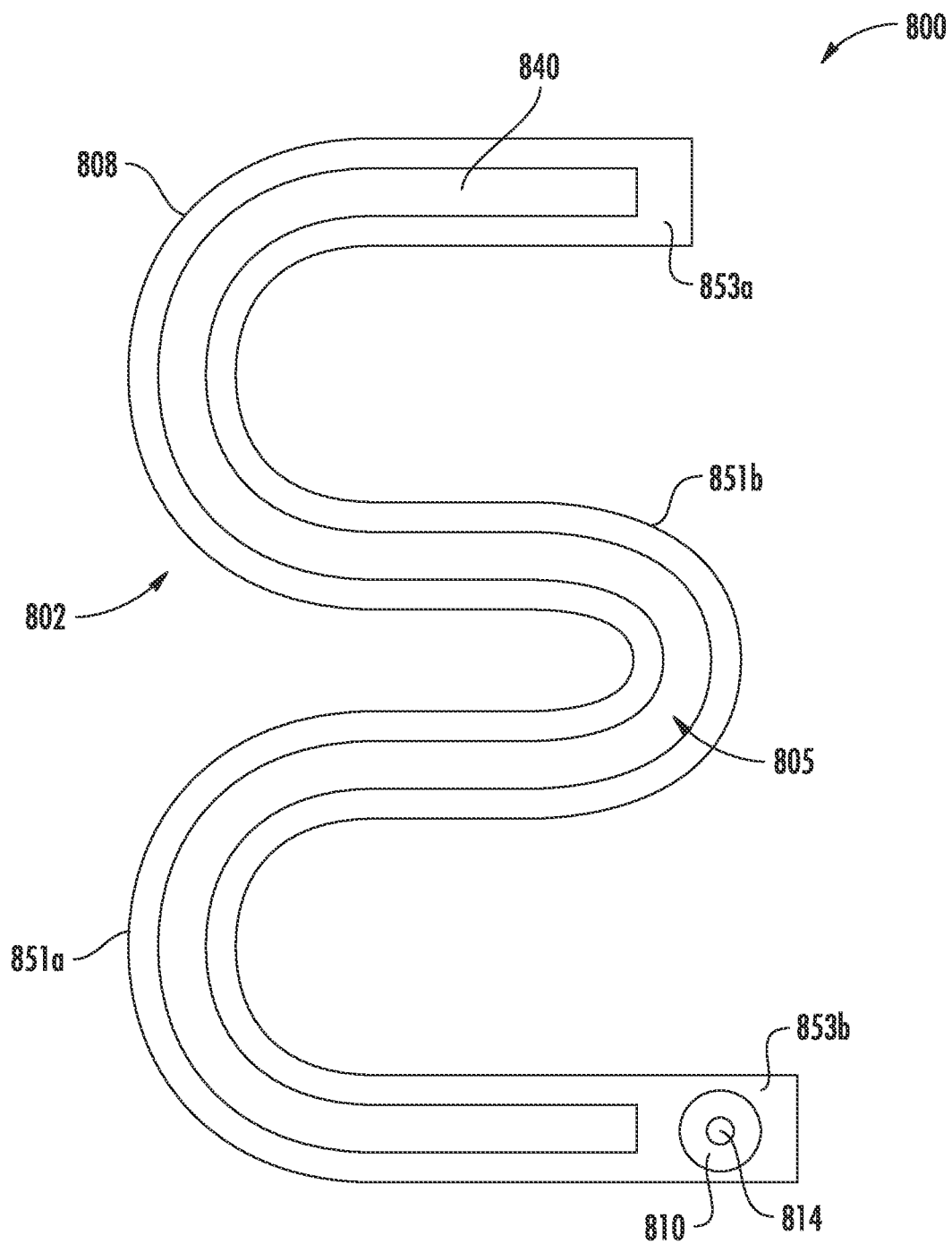
FIG. 8 is a cross-sectional view of another embodiment of a drug delivery device having a ribbon-shaped drug reservoir lumen, wherein the reservoir walls and lumen are in a serpentine configuration.

Still another embodiment of a drug delivery device having a ribbon-shaped drug reservoir lumen is depicted in FIG. 8. Drug delivery device 800 has a drug reservoir portion 802 which has an elongated body portion that includes a ribbon-shaped drug reservoir lumen 805. The lumen 805 is defined by and within reservoir walls 808, and the lumen 805 is substantially or completely filled with a drug formulation 840. The drug reservoir lumen is ribbon-shaped and the ribbon shaped lumen (as well as the reservoir walls defining it) is in an overall serpentine shape. The reservoir walls 808 include opposed long sidewalls 851a and 851b which are connect to (and typically integrally formed with) opposed short sidewalls 853a and 853b. Short sidewall 853b, in the illustrated embodiment, is thicker than short sidewall 853a and includes a retention frame lumen 810 in which retention frame 814 is disposed.

In one embodiment, the drug delivery devices having a ribbon-shaped drug reservoir lumen have a single ribbon-shaped drug reservoir lumen. In other embodiments, the drug delivery devices having a ribbon-shaped drug reservoir lumen may have two or more ribbon-shaped drug reservoir lumens. Not wishing to be bound by any particular theory, it is believed that using multiple ribbon-shaped drug reservoir lumens in a single device may be helpful for achieving a relatively uniform distribution of powder drug formulation along the length of the drug reservoir lumens. For example, a single drug delivery device having a ribbon-shaped drug reservoir lumen may contain 40 mg of a powder drug formulation dispersed in a drug reservoir lumen that is 15 cm long. Alternatively, a single drug delivery device also containing 40 mg of a powder drug may include four ribbon-shaped drug reservoir lumens, each containing 10 mg of powder drug formulation and having a length of 15/4 cm.

Drug Reservoir Portion

The drug reservoir portion includes the part of the device that forms at least one drug reservoir lumen. In embodiments, the drug reservoir portion includes at least one reservoir wall which defines the drug reservoir lumen. A drug formulation is contained within the drug reservoir lumen. The drug reservoir lumen may comprise an elastic tube. The tube, when viewed in cross-section, may be cylindrical, substantially cylindrical, non-cylindrical, or ribbon-shaped. The tube of a drug reservoir lumen may be substantially linear and in some cases may be substantially cylindrical with a circular cross-section, although square, triangle, hexagon, and other polygonal cross-sectional shapes can be used, among others.

In embodiments, the elastic tube is a polymeric tube, such as a silicone tube or a polyurethane tube, or a tube comprising a combination of different biocompatible and water-permeable polymeric materials, such as different polyurethanes. In one embodiment, the drug reservoir lumen of the device is defined by an elongated, elastic annular tube.

The tube wall thickness may be determined based on the mechanical properties and water- and/or drug-permeability of the tube material. For example, designs in which a tube wall is too thin may not have sufficient mechanical integrity, while a design in which a tube wall is too thick may experience an undesirably long induction time for initial drug release from the device.

The thickness and strength of certain portions of the drug reservoir portion also may be selected to maintain the retention shape when the device does not include a retention frame.

For example, the drug reservoir portion may include a "backbone" that holds the device in its retention shape. The "backbone" may be a thicker and/or stronger section of the material from which the drug reservoir portion is formed. The "backbone" may traverse the length of the drug reservoir portion, either linearly, spirally, or tortuously.

The drug reservoir lumen may be formed from an elastomeric material, which may permit elastically deforming the device for its insertion into a patient, e.g., during its deployment through deployment instrument such as a cystoscope or catheter. For example, the tube may be elastically deformed along with the retention frame for intravesical implantation.

In a preferred embodiment, the drug reservoir lumen is formed from a material that is both elastomeric and water permeable. One material that is both elastomeric and water permeable is silicone. Another material is Tecophilic, although other biocompatible materials may be used.

The drug reservoir portion may be made from materials that a biodegradable, non-biodegradable, or a combination thereof.

In some embodiments, the device does not include a retention frame, and the drug reservoir portion is capable of imparting a retention shape to the device. In a particular embodiment, the drug reservoir portion is formed with a material that is treated or altered so that the device is deformable between a retention shape and a deployment shape. For example, the material used to form the drug reservoir portion may "memorize" and spontaneously assume the relatively expanded shape upon the application of heat to the device, such as when exposed to body temperatures upon entering the bladder. In some instances, the heating may cause at least a portion of the polymeric material to cross-link so that the device is capable of retaining the retention shape upon deployment in the bladder.

The ends of the tube are generally sealed to limit escape of the drug, such as with a sealing structure or other sealing means. The sealing structure may have any shape suited to plug or close the tube end, such as a cylinder or ball. In some embodiments, the sealing structure may have a larger diameter than the inner diameter of the tube, such that the tube stretches to fit snugly about the sealing structure, closing the tube and retaining the sealing structure in place. The sealing structure may be formed from biocompatible material, including a metal such as stainless steel, a polymer such as silicone, a ceramic, sapphire, or adhesive, among others or combinations thereof. The material may be biodegradable or bioerodible. A medical grade silicone adhesive or other adhesive also may be loaded into the tube in a workable form and may then cure within the tube to seal the end.

In some embodiments, the drug reservoir portion may have multiple drug reservoirs. Each reservoir may be defined by a portion of the tube inner surface and at least one partition. The multiple reservoirs may permit segregating two or more different drugs in different reservoirs, or delivering a single drug from different reservoirs at different rates or times following deployment into the patient.

In one embodiment, the total volume of the reservoir (or combined reservoirs) and the core region is sufficient to contain all the drug needed for local delivery over the course of a single treatment, reducing the number of procedures needed to treat a particular condition.

In a preferred embodiment, the device operates essentially by diffusion of the drug from the drug reservoir through (i) one or more discrete apertures formed in the reservoir wall, or through passing pores formed in a porous reservoir wall; (ii) through the (non-porous) reservoir wall itself, which may be permeable to the drug; or (iii) a combination thereof. In embodiments in which diffusion occurs through the wall, the apertures or passing pores may not be included.

In another embodiment, the device may be adapted to operate by osmotic pressure, e.g., as an osmotic pump. In still other embodiment, the device may operate by a combination of osmosis and diffusion.

Retention Frame Portion

The drug delivery devices, in some embodiments, have a structure that is deformable between a retention shape and a low profile shape for deployment, implantation, or insertion. Suitable retention frames and configurations for intravesical tolerability are described in U.S. Pat. No. 8,679,094 to Cima et al., which is incorporated herein by reference.

The drug delivery device may include a retention frame portion. The retention frame portion is associated with the drug reservoir portion and permits retaining the drug reservoir portion in the body, such as in the bladder. The retention frame portion may include a retention frame that is operable to impart a retention shape to the device structure, and is deformable between a relatively expanded shape and a relatively lower-profile shape.

For example, the retention frame may naturally assume the relatively expanded shape, may be manipulated into the relatively lower-profile shape for insertion into the body, and may spontaneously return to the relatively expanded shape upon insertion into the body. The retention frame in the relatively expanded shape may be shaped for retention in a body cavity, and the retention frame in the relatively lower-profile shape may be shaped for insertion into the body through the working channel of a deployment instrument such as a catheter or cystoscope. To achieve such a result, the retention frame may have an elastic limit, modulus, and/or spring constant selected to impede the device from assuming the relatively lower-profile shape once implanted, inserted, or deployed. Such a configuration may limit or prevent accidental expulsion of the device from the body under expected forces. For example, the device may be retained in the bladder during urination or contraction of the detrusor muscle.

In embodiments, the device body may include a retention frame lumen, with the retention frame positioned in the retention frame lumen.

In a preferred embodiment, the retention frame includes or consists of an elastic wire. For example, in the embodiment shown in FIGS. 1A-1B, the retention frame 114 may be an elastic wire formed from a superelastic alloy, such as nitinol. Thus, the retention portion wall, which surrounds the retention frame, may be formed from a polymer material, such as silicone. In other embodiments, the retention frame may be an elastic wire formed from a relatively low modulus elastomer. Examples of low modulus elastomers include polyurethane, silicone, styrenic thermoplastic elastomer, and poly(glycerol-sebacate) (PGS). The elastic wire may be coated with a biocompatible polymer, such as a coating formed from one or more of silicone, polyurethane, styrenic thermoplastic elastomer, Silitek, Tecoflex, C-flex, and Percuflex.

In embodiments in which the retention frame comprises a shape-memory material, the material used to form the frame may "memorize" and spontaneously assume the relatively expanded shape upon the application of heat to the device, such as when exposed to body temperatures upon entering the bladder.

When the retention frame is in the relatively expanded shape, such as the coiled shape shown in FIG. 1A, the device may occupy a space having dimensions suited to impede expulsion from the bladder. When the retention frame is in the relatively lower-profile shape, the device may occupy an area suited for insertion into the body, such as through the working channel of a deployment instrument. The properties of the elastic wire cause the device to function as a spring, deforming in response to a compressive load but spontaneously returning to its initial shape once the load is removed.

The retention frame may be in a form having a high enough spring constant to retain the device within a body cavity, such as the bladder. A high modulus material may be used, or a low modulus material. Especially when a low-modulus material is used, the retention frame may have a diameter and/or shape that provide a spring constant without which the frame would significantly deform under the forces of urination. For example, the retention frame may include one or more windings, coils, spirals, or combinations thereof, specifically designed to achieve a desirable spring constant, such as a spring constant in the range of about 3 N/m to about 60 N/m, or more particularly, in the range of about 3.6 N/m to about 3.8 N/m. Such a spring constant may be achieved by one or more of the following techniques: increasing the diameter of the elastic wire used to form the frame, increasing the curvature of one or more windings of the elastic wire, and adding additional windings to the elastic wire. The windings, coils, or spirals of the frame may have a number of configurations. For example, the frame may be in a curl configuration comprising one or more loops, curls or sub-circles. The ends of the elastic wire may be adapted to avoid tissue irritation and scarring, such as by being soft, blunt, inwardly directed, joined together, or a combination thereof.

A retention frame that assumes a pretzel shape may be relatively resistant to compressive forces. The pretzel shape essentially comprises two sub-circles, each having its own smaller arch and sharing a common larger arch. When the pretzel shape is first compressed, the larger arch absorbs the majority of the compressive force and begins deforming, but with continued compression the smaller arches overlap, and subsequently, all three of the arches resist the compressive force. The resistance to compression of the device as a whole increases once the two sub-circles overlap, impeding collapse and voiding of the device as the bladder contracts during urination. The retention frame portion can be elastically deformed into the linear shape for deployment through a deployment instrument.

Drug Formulation

The drug formulation can include essentially any therapeutic, prophylactic, or diagnostic agent, such as one that would be useful to deliver locally or regionally to a desired tissue site. For example, the tissue site may include the urinary bladder, the prostate, etc.

The drug formulation may consist only of the drug, or one or more pharmaceutically acceptable excipients may be included. As used herein, the term "drug" with reference to any specific drug described herein includes its alternative forms, such as salt forms, free acid forms, free base forms, and hydrates. The drug may be a small molecule drug or a biologic. The drug may be a metabolite. Pharmaceutically acceptable excipients are known in the art and may include lubricants, viscosity modifiers, surface active agents, osmotic agents, diluents, and other non-active ingredients of the formulation intended to facilitate handling, stability, dispersibility, wettability, and/or release kinetics of the drug.

In an embodiment, the drug formulation is in a solid or semi-solid form in order to reduce the overall volume of the drug formulation and thereby reduce the size of the device, facilitating implantation, insertion, or deployment. The semi-solid form may be, for example, an emulsion or suspension; a gel or a paste. In many embodiments, the drug formulation desirably includes no or a minimum quantity of excipient for the same reasons of volume/size minimization.

In some embodiments, the drug is a high solubility drug. As used herein, the term "high solubility" refers to a drug having a solubility above about 10 mg/mL water at 37° C. In other embodiments, the drug is a low solubility drug. As used herein, the term "low solubility" refers to a drug having a solubility from about 0.01 mg/mL to about 10 mg/mL water at 37° C. The solubility of the drug may be affected at least in part by its form. For example, a drug in the form of a water soluble salt may have a high solubility, while the same drug in base form may have a low solubility. One example is lidocaine, which has a high solubility of about 680 mg/mL when in the form of a lidocaine hydrochloride monohydrate, a water-soluble salt, but has a low solubility of about 8 mg/mL when in the form of lidocaine base.

High solubility drugs may be suited for release due to an osmotic pressure gradient, such as via one or more apertures or passing pores through the device wall, while low solubility drugs may be suited for release via diffusion, such as directly through the device wall or through one or more apertures or passing pores in the device wall. For example, lidocaine base may be released via diffusion through a silicone wall without an aperture. Thus, the drug may be formulated to have a high or low solubility depending on the intended release mode. In one embodiment, the drug is formulated to improve its apparent solubility in the environment of its use, such as its apparent solubility in urine within the bladder.

In one embodiment, the devices provide pain relief to the patient. A variety of anesthetic agents, analgesic agents, and combinations thereof may be used. In embodiments, the device delivers one or more anesthetic agents. The anesthetic agent may be a cocaine analogue. In embodiments, the anesthetic agent is an aminoamide, an aminoester, or combinations thereof. Representative examples of aminoamides or amide-class anesthetics include articaine, bupivacaine, carticaine, cinchocaine, etidocaine, levobupivacaine, lidocaine, mepivacaine, prilocaine, ropivacaine, and trimecaine. Representative examples of aminoesters or ester-class anesthetics include amylocaine, benzocaine, butacaine, chloroprocaine, cocaine, cyclomethycaine, dimethocaine, hexylcaine, larocaine, meprylcaine, metabutoxycaine, orthocaine, piperocaine, procaine, proparacaine, propoxycaine, proxymetacaine, risocaine, and tetracaine. These anesthetics typically are weak bases and may be formulated as a salt, such as a hydrochloride salt, to render them water-soluble, although the anesthetics also can be used in free base or hydrate form. Other anesthetics, such as lontocaine, also may be used. The drug also can be an antimuscarinic compound that exhibits an anesthetic effect, such as oxybutynin or propiverine. The drug also may include other drugs described herein, alone or in combination with an anesthetic agent.

In certain embodiments, the analgesic agent includes an opioid. Representative examples of opioid agonists include alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. Other opioid drugs, such as mu, kappa, delta, and nociception opioid receptor agonists, are contemplated.

Representative examples of other suitable pain relieving agents include such agents as salicyl alcohol, phenazopyridine hydrochloride, acetaminophen, acetylsalicylic acid, flufenisal, ibuprofen, indoprofen, indomethacin, naproxen.

In certain embodiments, the drug delivery device is used to treat inflammatory conditions such as interstitial cystitis, radiation cystitis, painful bladder syndrome, prostatitis, urethritis, post-surgical pain, and kidney stones. Non-limiting examples of specific drugs for these conditions include lidocaine, glycosaminoglycans (e.g., chondroitin sulfate, sulodexide), pentosan polysulfate sodium (PPS), dimethyl sulfoxide (DMSO), oxybutynin, mitomycin C, heparin, flavoxate, ketorolac, or a combination thereof. For kidney stones, the drug(s) may be selected to treat pain and/or to promote dissolution of renal stones.

Other non-limiting examples of drugs that may be used in the treatment of IC include nerve growth factor monoclonal antibody (MAB) antagonists, such as Tanezumab, and calcium channel alpha-2-delta modulators, such as PD-299685 or gabepentin.

Other intravesical cancer treatments include small molecules, such as Apaziquone, adriamycin, AD-32, doxorubicin, doxetaxel, epirubicin, gemcitabine, HTI-286 (hemiasterlin analogue), idarubicin, γ-linolenic acid, mitozantrone, meglumine, and thiotepa; large molecules, such as Activated macrophages, activated T cells, EGF-dextran, HPC-doxorubicin, IL-12, IFN-α2b, IFN-γ, α-lactalbumin, p53 adenovector, TNFα; combinations, such as Epirubicin+BCG, IFN+farmarubicin, Doxorubicin+5-FU (oral), BCG+IFN, and Pertussis toxin+cystectomy; activated cells, such as macrophages and T cells; intravesical infusions such as IL-2 and Doxorubicin; chemosensitizers, such as BCG+antifirinolytics (paramethylbenzoic acid or aminocaproic acid) and Doxorubicin+verapimil; diagnostic/imaging agents, such as Hexylaminolevulinate, 5-aminolevulinic acid, Iododexyuridine, HMFG1 Mab+Tc99m; and agents for the management of local toxicity, such as Formaline (hemorrhagic cystitis).

In one embodiment, the drug delivery device is used in association with the placement of a ureteral stent, such as to treat pain, urinary urgency or urinary frequency resulting from ureteral stent placement. Non-limiting examples of specific drugs for such treatment include anti-muscarinics, beta-blockers, narcotics, and phenazopyridine, among others.

The drug delivery device can be used, for example, to treat urinary incontinence, frequency, or urgency, including urge incontinence and neurogenic incontinence, as well as trigonitis. Drugs that may be used include anticholinergic agents, antispasmodic agents, anti-muscarinic agents, β-2 agonists, alpha adrenergics, anticonvulsants, norepinephrine uptake inhibitors, serotonin uptake inhibitors, calcium channel blockers, potassium channel openers, and muscle relaxants. Representative examples of suitable drugs for the treatment of incontinence include oxybutynin, S-oxybutytin, emepronium, verapamil, imipramine, flavoxate, atropine, propantheline, tolterodine, rociverine, clenbuterol, darifenacin, terodiline, trospium, hyoscyamin, propiverine, desmopressin, vamicamide, clidinium bromide, dicyclomine HCl, glycopyrrolate aminoalcohol ester, ipratropium bromide, mepenzolate bromide, methscopolamine bromide, scopolamine hydrobromide, iotropium bromide, fesoterodine fumarate, YM-46303 (Yamanouchi Co., Japan), lanperisone (Nippon Kayaku Co., Japan), inaperisone, NS-21 (Nippon Shinyaku Orion, Formenti, Japan/Italy), NC-1800 (Nippon Chemiphar Co., Japan), Z D-6169 (Zeneca Co., United Kingdom), and stilonium iodide.

In another embodiment, the drug delivery device is used to treat urinary tract cancer, such as bladder cancer and prostate cancer. Drugs that may be used include antiproliferative agents, cytotoxic agents, chemotherapeutic agents, or a combination thereof. Representative examples of drugs which may be suitable for the treatment of urinary tract cancer include Bacillus Calmette Guerin (BCG) vaccine, cisplatin, doxorubicin, valrubicin, gemcitabine, mycobacterial cell wall-DNA complex (MCC), methotrexate, vinblastine, thiotepa, mitomycin, fluorouracil, leuprolide, diethylstilbestrol, estramustine, megestrol acetate, cyproterone, flutamide, a selective estrogen receptor modulators (i.e. a SERM, such as tamoxifen), botulinum toxins, and cyclophosphamide. The drug may be a biologic, and it may comprise a monoclonal antibody, a TNF inhibitor, an antileukin, or the like. The drug also may be an immunomodulator, such as a TLR agonist, including imiquimod or another TLR7 agonist. The drug also may be a kinase inhibitor, such as a fibroblast growth factor receptor-3 (FGFR3)-selective tyrosine kinase inhibitor, a phosphatidylinositol 3 kinase (PI3K) inhibitor, or a mitogen-activated protein kinase (MAPK) inhibitor, among others or combinations thereof. Other examples include celecoxib, erolotinib, gefitinib, paclitaxel, polyphenon E, valrubicin, neocarzinostatin, apaziquone, Belinostat, Ingenol mebutate, Urocidin (MCC), Proxinium (VB 4845), BC 819 (BioCancell Therapeutics), Keyhole limpet haemocyanin, LOR 2040 (Lorus Therapeutics), urocanic acid, OGX 427 (OncoGenex), and SCH 721015 (Schering-Plough). The drug treatment may be coupled with a conventional radiation or surgical therapy targeted to the cancerous tissue.

In another embodiment, the drug delivery device is used to treat infections involving the bladder, the prostate, and the urethra. Antibiotics, antibacterial, antifungal, antiprotozoal, antiseptic, antiviral and other antiinfective agents can be administered for treatment of such infections. Representative examples of drugs for the treatment of infections include mitomycin, ciprofloxacin, norfloxacin, ofloxacin, methanamine, nitrofurantoin, ampicillin, amoxicillin, nafcillin, trimethoprim, sulfonamides trimethoprimsulfamethoxazole, erythromycin, doxycycline, metronidazole, tetracycline, kanamycin, penicillins, cephalosporins, and aminoglycosides.

In other embodiments, the drug delivery device is used to treat fibrosis of a genitourinary site, such as the bladder or uterus. Representative examples of drugs for the treatment of fibroids include pentoxphylline (xanthine analogue), antiTNF, antiTGF agents, GnRH analogues, exogenous progestins, antiprogestins, selective estrogen receptor modulators, danazol and NSAIDs.

The drug delivery device also may be used to treat neurogenic bladder. Representative examples of drugs for the treatment of neurogenic bladder include analgesics or anaesthetics, such as lidocaine, bupivacaine, mepivacaine, prilocaine, articaine, and ropivacaine; anticholinergics; antimuscarinics such as oxybutynin or propiverine; a vanilloid, such as capsaicin or resiniferatoxin; antimuscarinics such as ones that act on the M3 muscarinic acetylcholine receptor (mAChRs); antispasmodics including $GABA_B$ agonists such as baclofen; botulinum toxins; capsaicins; alpha-adrenergic antagonists; anticonvulsants; serotonin reuptake inhibitors such as amitriptyline; and nerve growth factor antagonists. In various embodiments, the drug may be one that acts on bladder afferents or one that acts on the efferent cholinergic transmission, as described in Reitz et al., *Spinal Cord* 42:267-72 (2004).

In one embodiment, the drug is selected from those known for the treatment of incontinence due to neurologic detrusor overactivity and/or low compliant detrusor. Examples of these types of drugs include bladder relaxant drugs (e.g., oxybutynin (antimuscarinic agent with a pronounced muscle relaxant activity and local anesthetic activity), propiverine, impratroprium, tiotropium, trospium, terodiline, tolterodine, propantheline, oxyphencyclimine, flavoxate, and tricyclic antidepressants; drugs for blocking nerves innervating the bladder and urethra (e.g., vanilloids (capsaicin, resiniferatoxin), botulinum-A toxin); or drugs that modulate detrusor contraction strength, micturition reflex, detrusor sphincter dyssynergia (e.g., GABAb agonists (baclofen), benzodiazapines). In another embodiment, the drug is selected from those known for the treatment of incontinence due to neurologic sphincter deficiency. Examples of these drugs include alpha adrenergic agonists, estrogens, beta-adrenergic agonists, tricyclic antidepressants (imipramine, amitriptyline). In still another embodiment, the drug is selected from those known for facilitating bladder emptying (e.g., alpha adrenergic antagonists (phentolamine) or cholinergics). In yet another embodiment, the drug is selected from among anticholinergic drugs (e.g., dicyclomine), calcium channel blockers (e.g., verapamil) tropane alkaloids (e.g., atropine, scopolamine), nociceptin/orphanin FQ, and bethanechol (e.g., m3 muscarinc agonist, choline ester).

In an embodiment, the drug formulation is in solid form. For example, the drug formulation is formed into a powder, granules, or solid drug units that are loaded into the drug reservoir portion. Each of the drug units is a solid, discrete object that substantially retains a selectively imparted shape (at the temperature and pressure conditions to which the delivery device normally will be exposed during assembly, storage, and handling before implantation, insertion, or deployment). The drug units may be in the form of a powder, tablets, pellets, or beads, although other configurations are possible.

The drug tablets may be made by a direct compression tableting process, a molding process, or other processes known in the pharmaceutical arts. The tablets optionally may be coated with one or more materials known in the art for protecting the tablets against destructive exposure to oxygen or humidity during tablet handling, device assembly and storage; for facilitating device loading; for aesthetics; or for facilitating, retarding, or otherwise controlling in vivo dissolution and drug release characteristics.

The drug formulation may include a drug content and an excipient content. For example, the drug content may include one or more active pharmaceutical ingredients (APIs), while the excipient content includes one or more pharmaceutically acceptable excipients known in the art. Representative examples of such excipients include ingredients such as binders, lubricants, glidants, disintegrants, colors, fillers or diluents, coatings and preservatives, as well as other ingredients to facilitate manufacturing, storing, or administering the drug formulation.

In order to maximize the amount of drug that can be stored in and released from a given drug delivery device of a selected (small) size, the drug formulation preferably comprises a high weight fraction of drug or API, with a reduced or low weight fraction of excipients as are required for manufacturing and device assembly and use considerations. For the purposes of this disclosure, terms such as "weight fraction," "weight percentage," and "percentage by weight" with reference to drug, or API, refers to the drug or API in the form employed, such as in salt form, free acid form, free base form, or hydrate form. For example, a drug tablet that has 90% by weight of a drug in salt form may include less than 90% by weight of that drug in free base form.

In one embodiment, the drug formulation is more than 50% by weight drug. In a preferred embodiment, 75% or more of the weight of the drug formulation is drug, with the remainder of the weight comprising excipients, such as lubricants and binders that facilitate making the drug formulation, including a powder or tablet. For the purposes of this disclosure, the term "high weight fraction" with reference to the drug or API means that excipients constitute less than 25 wt %, preferably less than 20 wt %, more preferably less than 15 wt %, and even more preferably less than 10 wt % of the drug formulation. In some cases, the drug content comprises about 75% or more of the weight of the drug formulation. More particularly, the drug content may comprise about 80% or more of the weight of the drug formulation. For example, the drug content may comprise between about 85% and about 99.9% of the weight of the drug formulation. In some embodiments, the excipient content can be omitted completely.

In one embodiment, the drug and excipients are selected and formulated to be water soluble, so that the drug formulation can be solubilized when the device is located within the urinary bladder or other tissue site, to release the solubilized drug.

The individual drug units may have essentially any selected shape and dimension that fits within the reservoir lumen between the core region and the wall of the drug reservoir of the device.

The drug units, which may be hollow, may have outer dimensions that are about the same as, are slightly less than, or slightly exceed inner dimensions of the drug reservoir lumen.

In embodiments, the drug units, which may be hollow, are shaped to align in a row when housed in the drug reservoir. Each drug unit has a cross-sectional shape that corresponds to the cross-sectional shape of the drug reservoir, and each drug unit may have end face shapes that correspond to the end faces of adjacent drug units. Thus, once the drug tablets are loaded in the drug reservoir, the line or row of drug tablets may substantially fill the drug reservoir with interstices or breaks formed between adjacent drug units. The interstices or breaks accommodate deformation or movement of the device, such as during deployment, while permitting the individual drug units to retain their solid form. Thus, the drug delivery device may be relatively flexible or deformable despite being loaded with a solid drug, as each drug unit may be permitted to move with reference to adjacent drug units.

In a preferred embodiment, the drug formulations are formulated to be sterilizable, either within or outside of the drug delivery device, without substantial or detrimental changes in the chemical or physical composition of the drug formulation. The drug formulation can be sterilized before or after loading/assembly into a drug delivery device, and the drug formulations possess a commercially reasonable shelf life. Once implanted, deployed, or inserted, the composition of the drug formulation is appropriate for the intended route of administration, is stable in acidic conditions, and provides pre-selected, reproducible drug release kinetics. For example, the drug formulation may be solubilized in the bladder to continuously release drug at a suitably stable rate drug over an extended period.

Although several drug formulations are described above as having a high weight fraction of drug or API and a low weight fraction of excipients, the drug formulations may have any weight fraction of drug, especially in cases in which the drug formulation includes a drug that is extremely potent, a stabilizing agent, or an agent that increases the solubility of the drug, among others or combinations thereof.

Other Device Features

The device may include a retrieval string to facilitate withdrawal of a device from the patient. For example, the retrieval string may extend (or be selectively extendable) from the patient's urethra to facilitate manual removal of the device residing the patient's bladder.

In one embodiment, the device includes at least one radio-opaque portion or structure to facilitate detection or viewing (e.g., by X-ray imaging or fluoroscopy) of the device by a medical practitioner as part of the implantation, insertion, or retrieval procedure. In one embodiment, the device is constructed, at least in part, of a material that includes a radio-opaque filler material, such as barium sulfate or another radio-opaque material known in the art. Some tubing may be made radio-opaque by blending radio-opaque fillers, such as barium sulfate or another suitable material, during the processing of the tubing. The radio-opaque material also may be associated with the retention frame. For example, a platinum wire may be wound about ends of the elastic wire and covered in smoothening material. Ultrasound imaging may be used. Fluoroscopy may be the preferred method during deployment/retrieval of the non-erodible device by providing accurate real-time imaging of the position and orientation of the device to the practitioner performing the procedure.

Combination of the Components

The drug reservoir portion and the retention frame portion are associated with each other to form the drug delivery device. A variety of different associations are envisioned. For example, the drug reservoir portion and the retention frame portion may be at least partially aligned. In other words, the drug reservoir portion may extend along a portion or the entire length of the retention frame portion, substantially parallel or coincident with the retention frame portion. An example of such an embodiment is shown in FIGS. 1A-1B. The elastic wire may be embedded in a reinforcement area that joins together multiple discrete tubes. The tubes may hold the same or different drug formulations and also may be formed from the same or different materials of construction, such as materials that differ in permeability to urine or other aqueous or bodily fluids.

In other embodiments, the drug reservoir portion may be attached to only portion of the retention frame. The drug reservoir portion may have first and second end portions that are attached to a portion of the retention frame. The end portions of the drug reservoir may terminate at the retention frame, the end portions may overlap the retention frame, or a combination thereof. The drug reservoir portion may be oriented with reference to the retention frame portion such that the drug reservoir portion lies within the perimeter of the retention frame portion, beyond the perimeter of the retention frame portion, or a combination thereof. Additionally, a number of drug reservoir portions may be associated with a single retention frame portion.

In other embodiments, the drug reservoir portion and the retention frame portion may be the same component in some embodiments. In such cases, the device may comprise a tube or ribbon-shaped reservoir formed in a configuration having a sufficient spring constant to retain the device in the body, as described above. Also, the drug reservoir portion may be wrapped around the retention frame portion, one or any number of times.

The embodiments described herein may be combined and varied to produce other drug delivery devices that fall within the scope of the present disclosure. For example, the drug reservoir portion may be attached to any portion of the retention frame portion in any manner. Multiple drug reservoir portions may be provided, a single drug reservoir portion may be partitioned, or a combination thereof, which may facilitate delivering multiple different drugs into the body, delivering different forms of drugs into the body, delivering drugs at varying rates into the body, or a combination thereof.

Furthermore, when the device is in the retention shape, the retention frame portion may have any orientation with reference to the drug reservoir portion, laying either inside, outside, above, or below the drug reservoir portion or moving with reference to the drug reservoir portion as the device moves through the site of use. For example, the device 100 includes a retention frame portion that lies inside the perimeter of the drug reservoir portion. In other embodiments, the device includes a retention frame portion that lies below the drug reservoir portion (such that the retention frame portion would not be visible in FIG. 1A). A particular orientation between the two portions can be maintained by filling the retention frame portion with a filling material, such as a silicone adhesive, after the retention frame is loaded. The filling material may cure or solidify to prevent movement of one portion with reference to the other. Other means of maintaining the orientation of the retention frame portion with reference to the drug reservoir portion also can be used.

In the embodiment shown in FIG. 1A, for example, the drug delivery device 100 is suited for delivering a drug into the bladder. The drug reservoir body 106 may have an inner diameter of about 1.3 to about 3.3 mm, such as about 1.5 to about 3.1 mm, an outer diameter of about 1.7 to about 3.7 mm, such as about 1.9 to about 3.4 mm, and a length of about 12 to 21 cm, such as about 14 to 16 cm. The drug reservoir lumen 106 may hold about 10 to 100 structural objects 112 in the core region.

Method of Making the Device

An embodiment of a method of making a drug delivery device may include forming a drug delivery device, forming one or more structural objects, providing or making a drug formulation in a desired form, such as a powder or tablet, and loading the one or more objects and the drug formulation into the drug delivery device. In embodiments, forming the drug delivery device may include forming a device body having a drug reservoir lumen, forming a retention frame, and associating the device body with the retention frame. In other embodiments, forming the drug delivery device may include forming a device body capable or maintaining a retention shape. In further embodiments, forming the drug delivery device may include one or more of the following sub-steps: forming a device body, and treating the device body so that it will maintain a retention shape.

Forming the device body may include forming a flexible body having reservoir walls that define a drug reservoir lumen and, if necessary, a retention frame lumen. For example, the device body may be formed by extruding or molding a polymer, such as silicone. In particular, forming the device body may include integrally forming two tubes or walls that are substantially aligned and adjoined along a longitudinal edge. Alternatively, the two lumens may be separately formed and attached to each other, such as with an adhesive. Other methods of forming the device body also may be employed.

Forming a retention frame may include forming an elastic wire from, for example, a superelastic alloy or shape-memory material and "programming" the elastic wire to naturally assume a relatively expanded shape. Heat treatment may be used to program the elastic wire to assume the expanded shape. For example, the retention frame may be formed by forming the elastic wire into a pretzel shape and heat treating the elastic wire at a temperature over 500° C. for a period over five minutes. In embodiments in which the retention frame comprises a low modulus elastomer, the step of forming the retention frame may comprising forming one or more windings, coils, loops or spirals in the frame so that the frame functions as a spring. For example, the retention frame may be formed by extrusion, liquid injection molding, transfer molding, or insert molding, among others. Similar techniques may be used to form a device body capable of assuming a retention shape without being associated with a retention frame.

Associating the device body with the retention frame may comprise inserting the retention frame into the retention frame lumen of the device body. In some embodiments, a distal end of the retention frame is blunted or is covered in a smooth ball of increased cross section during insertion of the retention frame into the lumen. The ball may facilitate driving the retention frame through the retention frame lumen without puncturing the wall of the device body. Also in some embodiments, the device body may be slightly compressed between two surfaces during the insertion of the retention frame. Compressing the device body elongates the opening into the retention frame lumen, facilitating loading.

In some embodiments, associating the device body with the retention frame further includes filling the retention frame lumen with a filling material after the retention frame is loaded. In other embodiments, associating the device body with the retention frame portion may comprise integrally forming the two portions together, such as by overmolding the device body about the retention frame.

Forming one or more apertures, if any, in the device body may include laser drilling or mechanically punching one or more holes in the device body.

Solid drug forms may be made by a direct compression tableting process, a molding process, a granulating process or other processes known in the pharmaceutical arts. The produced solid forms of the drug formulation then may be loaded into the drug reservoir lumen before or after the core region is configured to exclude the presence of the drug formulation.

Some steps or sub-steps of the method of making a drug delivery device may be performed in other orders or simultaneously. For example, the retention frame may be associated with the device body either before or after the drug formulation is loaded into the device body.

Use and Applications of the Device

The device may be implanted, inserted, or deployed at any desired site, including in the urinary bladder or other body cavity or lumen of a patient in need thereof. The drug delivery devices provided herein also may be configured for subcutaneous, intramuscular, intraocular, intraperitoneal, and/or intrauterine implantation. Subsequently, the device may release one or more drugs for the treatment of one or more conditions, locally to one or more tissues at the deployment site and/or regionally to other tissues distal from the deployment site. The release may be controlled over an extended period. Thereafter, the device may be retrieved, resorbed, excreted, or some combination thereof.

In one example, the device is inserted into a patient by passing the drug delivery device through a deployment instrument and releasing the device from the deployment instrument into the body. In cases in which the device is inserted into a body cavity such as the bladder, the device assumes a retention shape, such as an expanded or higher profile shape, once the device emerges from the deployment instrument into the cavity.

Once inserted, the device may release the drug. The device may provide extended, continuous, intermittent, or periodic release of a desired quantity of drug over a desired, predetermined time period. In embodiments, the device can deliver the desired dose of drug over an extended period, such as 12 hours, 24 hours, 5 days, 7 days, 10 days, 14 days, or 20, 25, 30, 45, 60, or 90 days, or more. The rate of delivery and dosage of the drug can be selected depending upon the drug being delivered and the disease or condition being treated.

In embodiments in which the device comprises a drug in a solid form, elution of drug from the device occurs following dissolution of the drug within the device. Bodily fluid enters the device, contacts the drug and solubilizes the drug, and thereafter the dissolved drug diffuses from the device or flows from the device under osmotic pressure or via diffusion. For example, the drug may be solubilized upon contact with urine in cases in which the device is inserted in the bladder.

The device may be deployed into the bladder of a patient in an independent procedure or in conjunction with another urological or other procedure or surgery, either before, during, or after the other procedure. The device may release one or more drugs that are delivered to local and/or regional tissues for therapy or prophylaxis, either peri-operatively, post-operatively, or both.

In an embodiment, the device is configured for intravesical insertion for use in the local administration of one or more drugs into the bladder to treat interstitial cystitis, radiation cystitis, pelvic pain, overactive bladder syndrome, bladder cancer, neurogenic bladder, neuropathic or non-neuropathic bladder-sphincter dysfunction, infection, post-surgical pain or other diseases, disorders, and conditions treated with drugs delivered to the bladder. The device may deliver drugs that improve bladder function, such as bladder capacity, compliance, and/or frequency of uninhibited contractions, that reduce pain and discomfort in the bladder or other nearby areas, or that have other effects, or combinations thereof. The bladder-deployed device also may deliver a therapeutically effective amount of one or more drugs to other genitourinary sites within the body, such as other locations within urological or reproductive systems of the body, including one or both of the kidneys, the urethra, one or both of the ureters, the penis, the testes, one or both of the seminal vesicles, one or both of the vas deferens, one or both of the ejaculatory ducts, the prostate, the vagina, the uterus, one or both of the ovaries, or one or both of the fallopian tubes, among others or combinations thereof. For example, the intravesical drug delivery device may be used in the treatment of kidney stones or fibrosis, erectile dysfunction, among other diseases, disorders, and conditions.

In some embodiments, the drug delivery device is deployed into the bladder of a patient for regional drug delivery to one or more nearby genitourinary sites. The device may release drug locally to the bladder and regionally to other sites near the bladder. Such delivery may provide an alternative to systemic administration, which may entail undesirable side effects or result in insufficient bioavailability of the drug.

The present invention may be further understood with reference to the following non-limiting examples.

Example 1—Diffusion of Drug from Different Devices

Several drug delivery devices were loaded with lidocaine base, and the in vitro release of the lidocaine base was measured. Lidocaine base was chosen as a model drug because it can diffuse or permeate through silicone. Silicone tubes (MED-4750, Nusil) having a 2.64 mm inner diameter and a wall thickness of 0.2 mm were used to make the devices of this example. The lidocaine base was present in the devices in either powder form or tablet form. Both ends of each drug reservoir of the devices were sealed with 0.5 cm of silicone adhesive.

Four types of devices were tested, and three devices of each type were tested (n=3). For each device, the drug reservoir length and the drug mass loaded into the reservoir of each device is shown in the following table:

| Device Type | Drug reservoir length (cm) | Drug mass (mg, Mean ± SD) |
| --- | --- | --- |
| 5 cm-powder dispersed | 5.0 | 36 ± 3 |
| 2 cm-powder dispersed | 1.9 | 38 ± 6 |
| 1 cm-powder packed | 1.0 | 42 ± 1 |
| 1 cm-compressed tablet | 0.7 | 41 ± 2 |

The drug packing density was highest for the 1 cm-compressed tablet device, and the drug packing density was lowest for the 5 cm-powder dispersed type. For the powder dispersed type devices, lidocaine powder was dispensed into the tube and scattered along the tube length, which was 2 or 5 cm, until the powder visually covered the inner surface of the tube along the length of the reservoir by massaging or tapping the tube. For the powder packed type devices, the powder was tamped down into the silicone tube. For the compressed tablet type device, a lidocaine base tablet was made by the direct powder compaction method and loaded into the tube.

Figure 9:
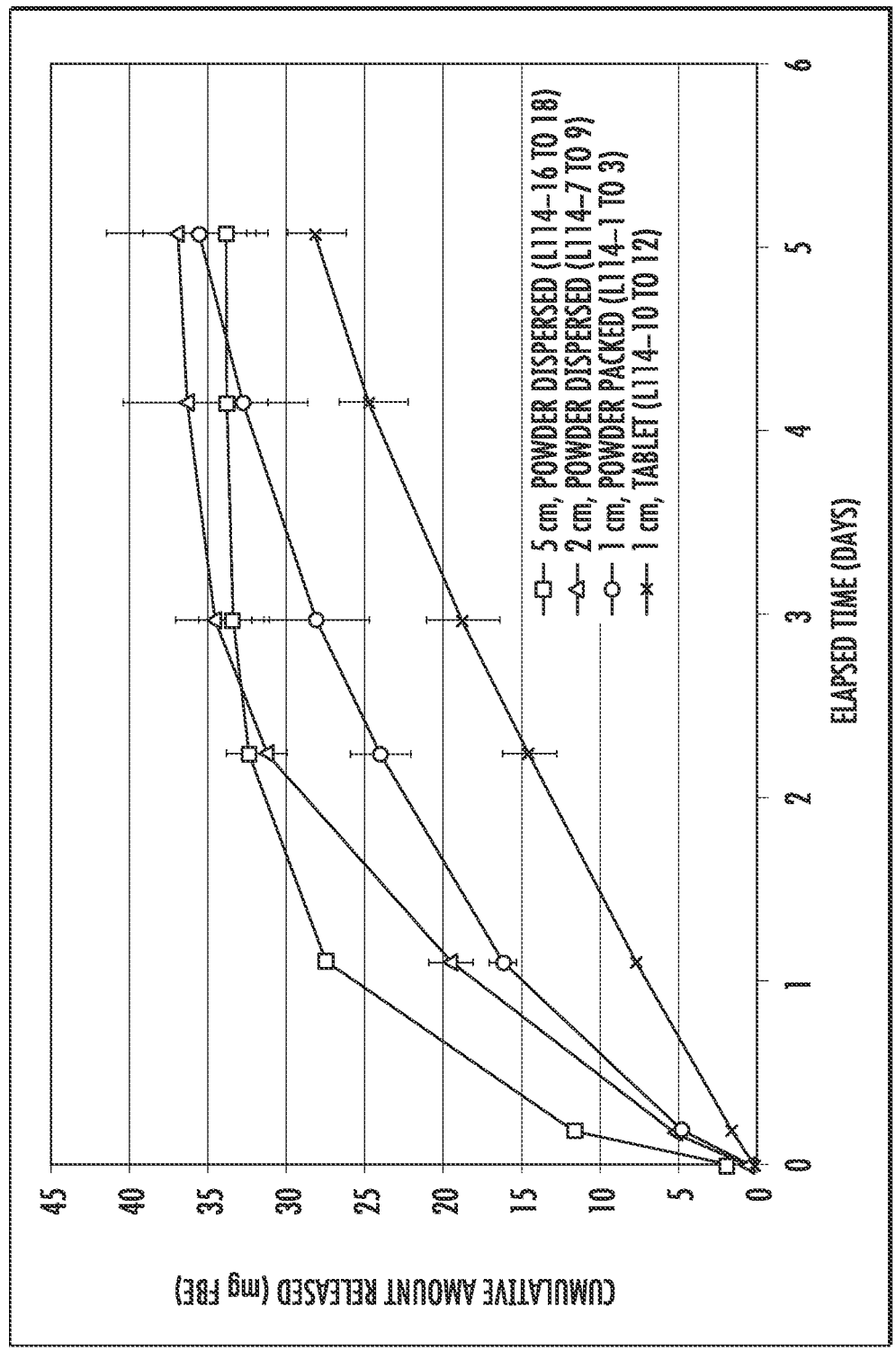
FIG. 9 is a graph which depicts a cumulative lidocaine amount released over time in vitro from various device configurations, as described in Example 1 below.

The cumulative amount of drug released over time (mg Free Base Equivalent (mg FBE)), is shown at FIG. 9. The error bars represent the standard deviations (SD) around the mean, which are not shown when smaller than the symbols. The release medium was 150 g of deionized water at 37° C., and the sample was collected daily and analyzed by HPLC. Until the drug payload was significantly depleted, the release was faster for the devices having longer drug reservoirs due to their diffusion surface areas, despite their lower drug packing density.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A drug delivery device for insertion into the body of a patient, the drug delivery device comprising:
    a drug reservoir portion which comprises a drug reservoir lumen bounded by reservoir walls which comprise a drug permeable and water permeable polymeric material;
    a retention frame lumen in which a retention frame is disposed; and
    a drug formulation which comprises a drug and which substantially fills the drug reservoir lumen,
    wherein the drug reservoir lumen has a ribbon shape such that a substantial portion of the drug formulation is adjacent to the reservoir walls to facilitate trans-wall diffusion of the drug through the reservoir walls, and
    wherein the drug delivery device is elastically deformable between a first shape configured to be inserted through a urethra into a bladder of the patient and a second shape, induced by the retention frame, configured to retain the entire drug delivery device within the bladder.

2. The drug delivery device of claim 1, wherein the reservoir walls are dimensioned to define the ribbon-shaped drug reservoir lumen to have a maximum width:maximum height ratio of at least 4:1.

3. The drug delivery device of claim 1, wherein the reservoir walls are dimensioned to define the ribbon-shaped drug reservoir lumen to have a maximum width:maximum height ratio of at least 7:1.

4. The drug delivery device of claim 1, wherein the reservoir walls are dimensioned to define the ribbon-shaped drug reservoir lumen to have a maximum width:maximum height ratio of at least 10:1.

5. The drug delivery device of claim 1, wherein the second shape is a coil shape, a spiral shape, or a serpentine shape.

6. The drug delivery device of claim 1, wherein the drug formulation is in the form of a powder or granules.

7. The drug delivery device of claim 1, wherein the reservoir walls comprise a water-permeable elastomeric material.

8. The drug delivery device of claim 7, wherein the water-permeable elastomeric material comprises silicone, a polyurethane, or a combination thereof.

9. The drug delivery device of claim 1, wherein the drug formulation is in the form of a powder or granules, and the reservoir walls comprise a water-permeable elastomeric material and are dimensioned to define the ribbon-shaped drug reservoir lumen having a maximum width:maximum height ratio of at least 4:1.

10. The drug delivery device of claim 1, wherein the reservoir walls comprise the retention frame lumen in which the retention frame is disposed.

11. The drug delivery device of claim 1, wherein the reservoir walls define an exterior surface of the drug delivery device.

12. A method of administering a drug to a patient in need thereof, comprising:
    inserting into the patient the drug delivery device of claim 1; and
    permitting the drug to be released from the drug delivery device.

13. The method of claim 12, wherein the drug delivery device is inserted into the patient's urinary bladder via through the patient's urethra.

14. An intravesical drug delivery device, the intravesical drug delivery device comprising:

a drug reservoir portion which comprises a drug reservoir lumen bounded by reservoir walls which comprise a drug permeable and water permeable elastomeric material; and a drug formulation in a solid form, which comprises a drug and which substantially fills the drug reservoir lumen, wherein the drug reservoir lumen has a ribbon shape such that a substantial portion of the drug formulation is adjacent to the reservoir walls to facilitate trans-wall diffusion of the drug through the reservoir walls, wherein the intravesical drug delivery device is elastically deformable between a first shape, which is a relatively straightened shape configured to be inserted through a patient's urethra, and a second shape, which is configured to retain the intravesical drug delivery device within the patient's bladder, and wherein the reservoir walls are dimensioned to define the ribbon-shaped drug reservoir lumen to have a maximum width:maximum height ratio of at least 4:1.

15. The intravesical drug delivery device of claim 14, wherein the second shape is a coil shape, a spiral shape, or a serpentine shape.

16. The intravesical drug delivery device of claim 14, wherein the reservoir walls define an exterior surface of the intravesical drug delivery device.

17. The intravesical drug delivery device of claim 14, further comprising a retention frame lumen in which a retention frame is disposed.

\* \* \* \* \*